US009205170B2

(12) United States Patent
Lucchesi et al.

(10) Patent No.: US 9,205,170 B2
(45) Date of Patent: Dec. 8, 2015

(54) WOUND DRESSING DEVICES AND METHODS

(75) Inventors: Lisa Lucchesi, Portland, OR (US); Hua Xie, Portland, OR (US)

(73) Assignee: HEMCON MEDICAL TECHNOLOGIES, INC., Portland, OR (US)

(*) Notice: Subject to any disclaimer, the term of this patent is extended or adjusted under 35 U.S.C. 154(b) by 420 days.

(21) Appl. No.: 12/387,378

(22) Filed: May 1, 2009

(65) Prior Publication Data

US 2010/0172958 A1    Jul. 8, 2010

Related U.S. Application Data

(60) Provisional application No. 61/049,831, filed on May 2, 2008.

(51) Int. Cl.
*A61L 15/28* (2006.01)

(52) U.S. Cl.
CPC ...................................... *A61L 15/28* (2013.01)

(58) Field of Classification Search
None
See application file for complete search history.

(56) References Cited

U.S. PATENT DOCUMENTS

| | | |
|---|---|---|
| 2,610,625 A | 9/1952 | Sifferd et al. |
| 2,858,830 A | 11/1958 | Robins |
| 2,923,664 A | 2/1960 | Cook et al. |
| 3,551,556 A | 12/1970 | Kliment et al. |
| 3,632,754 A | 1/1972 | Balassa |
| 3,800,792 A | 4/1974 | McKnight et al. |
| 3,801,675 A | 4/1974 | Russell |
| 3,849,238 A | 11/1974 | Gould et al. |
| 3,902,497 A | 9/1975 | Casey |
| 3,911,116 A | 10/1975 | Balassa |
| 3,954,493 A | 5/1976 | Battista et al. |
| 3,977,406 A | 8/1976 | Roth |
| 4,040,884 A | 8/1977 | Roth |
| 4,056,103 A | 11/1977 | Kaczmarzyk |
| 4,068,757 A | 1/1978 | Casey |
| 4,094,743 A | 6/1978 | Leuba |
| 4,195,175 A | 3/1980 | Peniston et al. |
| 4,292,972 A | 10/1981 | Palwelchak et al. |
| 4,373,519 A | 2/1983 | Errede et al. |
| 4,394,373 A | 7/1983 | Malette et al. |
| 4,452,785 A | 6/1984 | Malette et al. |
| 4,460,642 A | 7/1984 | Errede et al. |
| 4,501,835 A | 2/1985 | Berke |
| 4,524,064 A | 6/1985 | Nambu |
| 4,532,134 A | 7/1985 | Malette et al. |
| 4,533,326 A | 8/1985 | Anthony |
| 4,541,426 A | 9/1985 | Webster |
| 4,599,209 A | 7/1986 | Dautzenberg et al. |
| 4,651,725 A | 3/1987 | Kifune et al. |
| 4,684,370 A | 8/1987 | Barrett |
| 4,699,135 A | 10/1987 | Motosugi et al. |
| 4,759,348 A | 7/1988 | Cawood |
| 4,772,419 A | 9/1988 | Malson et al. |
| 4,833,237 A | 5/1989 | Kawamura et al. |
| 4,948,540 A | 8/1990 | Nigam |
| 4,952,618 A | 8/1990 | Olsen |
| 4,956,350 A | 9/1990 | Mosbey |
| 4,958,011 A | 9/1990 | Bade |
| 4,960,413 A | 10/1990 | Sagar et al. |
| 4,973,493 A | 11/1990 | Guire |
| 4,977,892 A | 12/1990 | Ewall |
| 5,006,071 A | 4/1991 | Carter |
| 5,024,841 A | 6/1991 | Chu et al. |
| 5,035,893 A | 7/1991 | Shioya et al. |
| 5,062,418 A * | 11/1991 | Dyer et al. ..................... 602/45 |
| 5,110,604 A | 5/1992 | Chu et al. |
| 5,116,824 A | 5/1992 | Miyata et al. |
| 5,154,928 A | 10/1992 | Andrews |
| 5,206,028 A | 4/1993 | Li |
| 5,254,301 A | 10/1993 | Sessions et al. |
| 5,300,494 A | 4/1994 | Brode, II et al. |
| 5,376,376 A | 12/1994 | Li |
| 5,378,472 A | 1/1995 | Muzzarelli |
| 5,420,197 A | 5/1995 | Lorenz et al. |
| 5,454,719 A | 10/1995 | Hamblen |
| 5,525,710 A | 6/1996 | Unger et al. |

(Continued)

FOREIGN PATENT DOCUMENTS

| | | |
|---|---|---|
| EP | 0353972 | 2/1990 |
| EP | 0477979 | 9/1991 |

(Continued)

OTHER PUBLICATIONS

PCT Notification of Transmittal of International Preliminary Report on Patentability; PCT/US09/02723, Aug. 16, 2010.
Park et al., "Platelet derived growth factor releasing chitosan sponge for periodontal bone regeneration." Biomaterials, vol. 21: 153-159, 2000.
Allan et al., "Biomedical Applications of Chitin and Chitosan." Chitin, Chitosan, and Related Enzymes—Accademic Press, Inc.: 119-133, 1984.
Anema et al., "Potential Uses of Absorbable Fibrin Adhesive Bandage for Genitourinary Trauma." World Journal of Surgery, vol. 25: 1573-1577, 20.
Bégin et al., "Antimicrobial films produced from chitosan." International Journal of Biological Macromolecules, vol. 26: 63-67, 1999.
Belman et al., "From the Battlefield to the Street." Per declaration submitted in U.S. Appl. No. 10/480,827, dated Dec. 17, 2007, poster presentation was made at the ATACCC Conference, Aug. 2006.

(Continued)

*Primary Examiner* — Bethany Barham
*Assistant Examiner* — Peter Anthopolos
(74) *Attorney, Agent, or Firm* — Chandra E. Eidt; Miller Nash Graham & Dunn LLP

(57) ABSTRACT

The present invention provides an absorbent wound dressing assembly that can be used to stanch, seal, or stabilize a site of tissue injury, tissue trauma, or tissue access. The wound dressing assembly is flexible so that it can be adapted and used to fit in narrow and small wound sites. Generally the wound dressing assembly comprises a flexible carrier material that is impregnated with a non-mammalian material for control of severe bleeding. The preferred non-mammalian material is poly [β-(1→4)-2-amino-2-deoxy-D-glucopyranose] more commonly referred to as chitosan.

6 Claims, 30 Drawing Sheets

(56) References Cited

U.S. PATENT DOCUMENTS

| | | |
|---|---|---|
| 5,571,181 A | 11/1996 | Li |
| 5,597,581 A | 1/1997 | Kaessmann et al. |
| 5,643,596 A | 7/1997 | Pruss et al. |
| 5,700,476 A | 12/1997 | Rosenthal et al. |
| 5,738,860 A | 4/1998 | Schonfeldt |
| 5,756,111 A | 5/1998 | Yoshikawa et al. |
| 5,765,682 A | 6/1998 | Bley et al. |
| 5,797,960 A | 8/1998 | Stevens et al. |
| 5,821,271 A | 10/1998 | Roenigk |
| 5,827,265 A | 10/1998 | Glinsky et al. |
| 5,836,970 A | 11/1998 | Pandit |
| 5,840,777 A | 11/1998 | Eagles et al. |
| 5,858,292 A | 1/1999 | Dragoo et al. |
| 5,858,350 A | 1/1999 | Voumakis et al. |
| 5,952,618 A | 9/1999 | Deslauriers |
| 5,961,478 A | 10/1999 | Timmermans |
| 6,042,877 A | 3/2000 | Lyon et al. |
| 6,054,122 A | 4/2000 | MacPhee et al. |
| 6,103,369 A | 8/2000 | Lucast et al. |
| 6,124,273 A | 9/2000 | Drohan et al. |
| 6,156,330 A | 12/2000 | Tsukada et al. |
| 6,162,241 A | 12/2000 | Coury et al. |
| 6,225,521 B1 | 5/2001 | Gueret |
| 6,270,515 B1 | 8/2001 | Linden et al. |
| 6,406,712 B1 | 6/2002 | Rolf |
| 6,448,462 B2 | 9/2002 | Groitzsch et al. |
| 6,454,787 B1 | 9/2002 | Maddalo et al. |
| 6,485,667 B1 | 11/2002 | Tan |
| 6,486,285 B2 | 11/2002 | Fujita |
| 6,548,081 B2 | 4/2003 | Sadozai et al. |
| 6,548,569 B1 | 4/2003 | Williams et al. |
| 6,552,244 B1 | 4/2003 | Jacques et al. |
| 6,565,878 B2 | 5/2003 | Schoenfeldt et al. |
| 6,566,577 B1 | 5/2003 | Addison et al. |
| 6,599,891 B2 | 7/2003 | North et al. |
| 6,693,180 B2 | 2/2004 | Lee et al. |
| 6,726,712 B1 | 4/2004 | Raeder-Devens et al. |
| 6,750,262 B1 | 6/2004 | Hähnle et al. |
| 6,855,860 B2 | 2/2005 | Ruszczak et al. |
| 6,863,924 B2 | 3/2005 | Ranganathan et al. |
| 6,864,245 B2 | 3/2005 | Voumakis et al. |
| 6,992,233 B2 | 1/2006 | Drake et al. |
| 7,019,191 B2 | 3/2006 | Looney et al. |
| 7,371,403 B2 | 5/2008 | McCarthy et al. |
| 7,402,172 B2 | 7/2008 | Chin et al. |
| 7,482,503 B2 | 1/2009 | Gregory et al. |
| 7,637,934 B2 | 12/2009 | Mangiardi et al. |
| 7,671,102 B2 | 3/2010 | Gaserod et al. |
| 7,850,709 B2 | 12/2010 | Cummins et al. |
| 7,897,832 B2 | 3/2011 | McAdams et al. |
| 2001/0045177 A1 | 11/2001 | Harvey et al. |
| 2002/0035391 A1 | 3/2002 | Mikus et al. |
| 2002/0161376 A1 | 10/2002 | Barry et al. |
| 2005/0036955 A1 | 2/2005 | DeGould |
| 2005/0123581 A1 | 6/2005 | Ringeisen et al. |
| 2005/0137512 A1 | 6/2005 | Campbell et al. |
| 2005/0143817 A1 | 6/2005 | Hunter et al. |
| 2005/0147656 A1* | 7/2005 | McCarthy et al. ............ 424/445 |
| 2005/0240137 A1 | 10/2005 | Zhu et al. |
| 2006/0004314 A1 | 1/2006 | McCarthy et al. |
| 2006/0008419 A1 | 1/2006 | Hissink et al. |
| 2006/0083710 A1 | 4/2006 | Joerger et al. |
| 2006/0184224 A1 | 8/2006 | Angel |
| 2006/0211973 A1 | 9/2006 | Gregory et al. |
| 2007/0021703 A1 | 1/2007 | McCarthy |
| 2007/0066920 A1 | 3/2007 | Hopman et al. |
| 2007/0066947 A1 | 3/2007 | Beck et al. |
| 2007/0083137 A1 | 4/2007 | Hopman et al. |
| 2007/0237811 A1 | 10/2007 | Scherr |
| 2007/0255194 A1 | 11/2007 | Gudnason et al. |
| 2007/0255243 A1 | 11/2007 | Kaun et al. |
| 2007/0276308 A1 | 11/2007 | Huey et al. |
| 2008/0064998 A1 | 3/2008 | Gregory et al. |
| 2008/0066663 A1 | 3/2008 | Easton et al. |
| 2008/0132990 A1 | 6/2008 | Richardson |
| 2008/0147019 A1 | 6/2008 | Song et al. |
| 2008/0241229 A1 | 10/2008 | Li et al. |

FOREIGN PATENT DOCUMENTS

| | | |
|---|---|---|
| EP | 0643963 | 3/1995 |
| EP | 1462123 | 9/2004 |
| JP | 60-142927 | 7/1985 |
| JP | 62-039506 | 2/1987 |
| JP | 63-090507 | 4/1988 |
| JP | 07-116241 | 5/1995 |
| JP | 11-342153 | 12/1999 |
| JP | 2002-233542 | 8/2002 |
| WO | WO 95/05794 | 3/1995 |
| WO | WO 98/48861 | 11/1998 |
| WO | WO 99/02587 | 1/1999 |
| WO | WO 00/56256 | 9/2000 |
| WO | WO 02/102276 | 12/2002 |
| WO | WO 03/047643 | 6/2003 |
| WO | WO 03/079946 | 10/2003 |
| WO | WO 03/092756 | 11/2003 |
| WO | WO 03/101310 | 12/2003 |
| WO | WO 2004/047695 | 6/2004 |
| WO | WO 2004/060412 | 7/2004 |
| WO | WO 2005062880 | 7/2005 |
| WO | WO 2006049463 | 5/2006 |
| WO | WO 2006071649 | 7/2006 |
| WO | WO 2006/079822 | 8/2006 |
| WO | WO 2007009050 | 1/2007 |
| WO | WO 2007056066 | 5/2007 |
| WO | WO 2007074327 | 7/2007 |
| WO | WO 2008033462 | 3/2008 |
| WO | WO 2008036225 | 3/2008 |

OTHER PUBLICATIONS

Chan et al., "Comparision of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage." The Journal of Trauma: 454-458, 2000.

CNN Transcript—3 pp., Jun. 8, 2006.

Cole et al., "A pilot study evaluating the efficacy of a fully acetylated poly-N-acetyl glucosamine membrane formulation as a topical hemostatic agent." Surgery, vol. 126, No. 3: 510-517, 1999.

HemCon Manufacturing Materials. Per declaration submitted in U.S. Appl. No. 10/480,827, dated Dec. 17, 2007, materials were submitted as supporting evidence for declaration.

Horesh et al., "Pre-hospital use of the HemCon bandage." Per declaration submitted in U.S. Appl. No. 10/480,827, dated Dec. 17, 2007, poster presentation was made at the WCDEM Conference, May 2007.

Kiley, Kevin, "Department of the Army memo." Jul. 20, 2005.

Kumar, Ravi, "Chitin and chitosan fibres: A review." Bulletin of Material Science: vol. 22, No. 5: 905-915, Aug. 1999.

Luo et al., "The role of poly(ethylene glycol) in the formation of silver nanoparticles." Journal of Colloid and Interface Science, vol. 288: 444-448, 2005.

Malette et al., "Chitosan: A New Hemostatic." The Annals of Thoratic Surgery, vol. 36, No. 1: 55-58, Jul. 1983.

Martin et al., "Medical applications of poly-4-hydroxybutyrate: a strong flexible absorbable biomaterial." Biochemical Engineering Journal, vol. 16: 97-105, 2003.

Mi et al., "Fabrication and characterization of a sponge-like asymmetric chitosan membrane as a wound dressing." . Biomaterials, vol. 22: 165-173, 2001.

Moody, Robin J., "HemCon bandage stakes claim to soldiers kit bag." Portland Business Journal, Nov. 4, 2005.

Ohshima et al., "Clinical Application of Chitin Non-Woven Fabric as Wound Dressing." European Journal of Plastic Surgery, vol. 10: 66-69, 1987.

Ohshima et al., "Clinical application of new chitin non-woven fabric and new chitin sponge sheet as wound dressing." European Journal of Plastic Surgery, vol. 14: 207-211, 1991.

Olsen et al., "Biomedical Applications of Chitin and its Derivatives." Chitin and Chitosan: Proceedings from the 4th International Conference on Chitin and Chitosan, 813-829, 1988.

(56) References Cited

OTHER PUBLICATIONS

Percot et al., "Optimization of Chitin Extraction from Shrimp Shells." Biomacromolecules, vol. 4: 12-18, 2003.
Pusateri et al., "Advanced Hemostatic Dressing Development Program: Animal Model Selection Criteria and Results of a Study of Nine Hemostatic Dressings in a Model of Severe Large Venous Hemorrhage and Hepatic Injury in Swine." The Journal of Trauma, vol. 55: 518-526, 2003.
Sandford, Paul A., "Chitosan: Commercial Uses and Potential Applications." Chitin and Chitosan: Proceedings from the 4th International Conference on Chitin and Chitosan, 51-69, 1988.
Sandford et al., "Biomedical Applications of High-Purity Chitosan." Water-Soluble Polymers: Chapter 28: 430-445, 1991.
Sandford, Paul A., "Biomedical Applications of New Forms of Chitin/Chitosan." Chitin Derivatives in Life Science, 12 pp., 1992.
Siekman, Philip, "A Shrimp Bandage?" Fortune Small Business, pp. 67-68, 2006.
Sondeen et al., "Comparison of 10 Different Hemostatic Dressings in an Aortic Injury." The Journal of Trauma, vol. 54, No. 2: 280-285, 2003.
Wedmore et al., "A Special Report on the Chitosan-based Hemostatic Dressing: Experience in Current Combat Operations." The Journal of Trauma, vol. 60: 655-658, 2006.
Wilson, J.R., "The Army's Greatest Inventions." U.S. Army Materiel Command, pp. 30-37, 2005.
Bendix., "Chemical synthesis of polyactide and its copolymers for medical applications." Polymer Degradation and Stability, vol. 59: 129-135, 1998.
Schoof et al., "Control of Pore Structure and Size in Freeze-Dried Collagen Sponges." Journal of Biomedical Material Research, vol. 58: 352-357, 2001.
Wu et al., "Development of in Vitro Adhesion Test for Chitosan Bandages." Society for Biomaterials 30th Annual Meeting Transactions, 2005, 1pg.
Database WPI, Week 200873 Thomson Scientific, London GB, an 2008-M34232, XP002695569 & CN 101138648, Mar. 12, 2008.

* cited by examiner

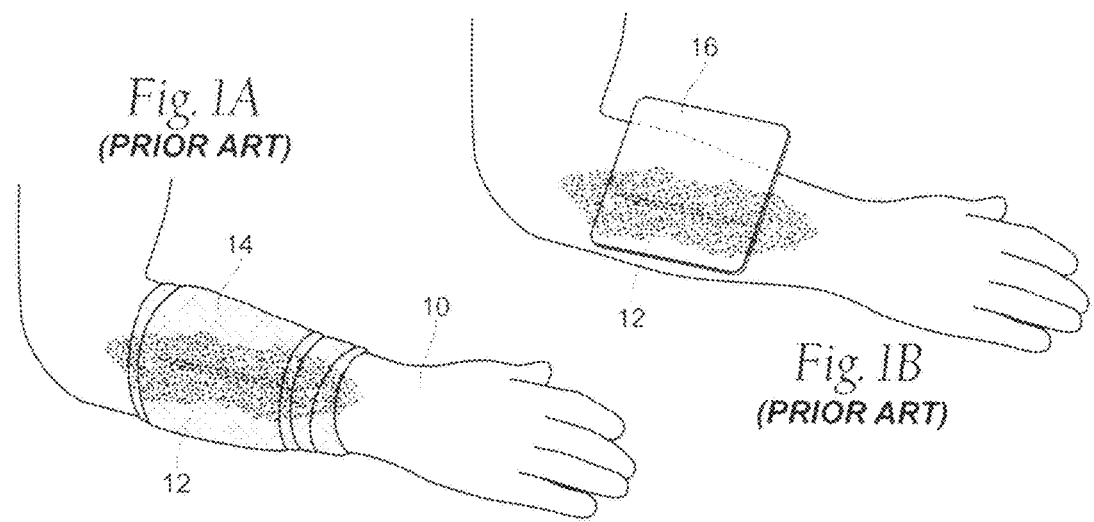
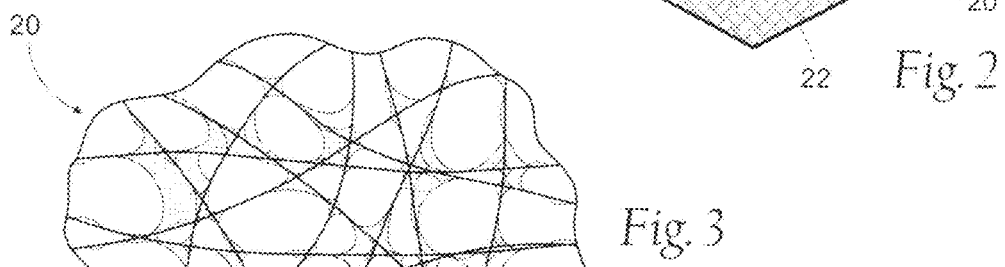
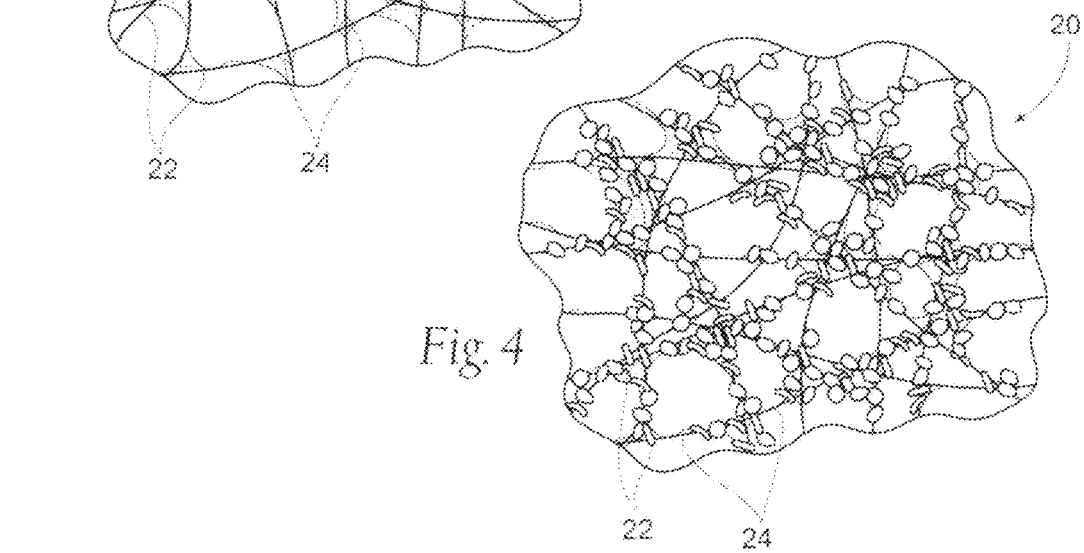

Scanning Electron Micrograph Images (SEM) (5X Resolution) of Wound Dressing Assemblies Containing Chitosan SEM Image of a Wound Dressing Assembly Comprising a Chitosan Material Magnified SEM Image of the Wound Dressing Assembly of Figure 18

Wound Dressing Assembly Comprising a 2% Chitosan Material

SEM Image of a Dressing Assembly
Prior to Interacting with Blood

SEM Image of Blood Interfacing With a
Dressing Assembly Containing a Chitosan Material

*Effect of Drying Temperature on Contact Angle for Wound Dressing Assemblies*

*Adhesion Strengths for Wound Dressing Assemblies Containing Various Amounts of Chitosan*

*Adhesion Strengths for Wound Dressing Assemblies Containing Various Amounts of Lactic Acid and a 2% Chitosan Material*

*Comparison of Stiffness of Various Wound Dressing Assemblies*

| Chitogauze (IMD) In Vitro - In Vivo Data as of 02.12.09 | | | Lap Pads | Controls | | 100808 |
| --- | --- | --- | --- | --- | --- | --- |
| | | | | J & J Kling roll (uncoated) | Combat Gauze | |
| Gauze | Gauze Mfg | | Cotton 4 ply (3 ply in spleen) | J & J Kling roll | Unknown | J & J Kling roll |
| | RP Blend | | NA | 30/70 | 50/50 assumed | 30/70 |
| | gsm | | NA | 55 | Unknown | 55 |
| | Notes | | NA | aperture, creped | sm ap | aperture, creped |
| In-Vitro Results | Gurley Stiffness | Length | 9 | 4 | 7 | 72 |
| | | Width | 21 | 4 | 3 | 35 |
| | | Product | 185 | 16 | 21 | 2520 |
| | Permeability | Application Score | 1 | 1 | 1 | 1 |
| | | mean flow rate, ml/sec (sd) | 0.7 (0.2) | 0.87 (0.2) | 1.15 (0.76) | 0.19 |
| | | Rebound | 0 | 10% | 0% | 10% |
| | Single Drop Absorption Time | length spreading? | 7 | 19.1 | 19.6 | 22 |
| | | Time to reach 5 μl sessile volume, sec (sd) | 1 | 8 | 0.5 | 59 (37) |
| | WBCT | % of neg control | | 47.4 | 16.6 | 74.4 |
| | | % difference of coated vs uncoated | | | N/A | -1 |
| | Absorbance Capacity (g/g) | | | 14 (0.2) | 8.6 (0.3) | 9.4 (0.6) |
| | Moisture (%) | | | 2.38 | 4.26 | 4.36 |
| | Acid (%) | | 0 | 0 | 0 | 1.93 |
| Spleen in-vivo | Pre-bleed Rate (g/min) | | 8.04 | | | |
| | 5 min Bleed Rate (g/min) | | 2.09 | | | |
| | % change in 5 min | | 29.17% | | | |
| | 10 min Bleed Rate (g/min) | | 0.75 | | | |
| | % change in 10 min | | 10.22% | | | |
| | Success in 5 min? | | 3/17 | | | |
| | t to hemostasis (min:sec) | | 5:61 | | | |
| ISR Femoral in-vivo | Study # (if any) | | RD142 | RD142 | RD193 | NA (add-ons) |
| | in vivo results | | 3/8 | 5/8 | 5/8 | 5/6 |
| | % 3-hr Survival | | 38% | 63% | 63% | 83% |
| | 1st app successes | | 2/8 | 2/8 | 2/8 | 5/6 |
| | % 1st app successes | | 25% | 25% | 25% | 83% |
| | Immediate hemostasis | | 2/3 | 4/5 | 2/8 | |
| | % Immediate hemostasis | | 66.7% | 80% | 25% | |
| | Success over total # of apps | | 3/15 | 5/13 | 5/14 | 5/7 |
| | % success of total # of apps | | 20% | 38% | 36% | 71% |
| | Avg pig wt. (kg) | | 39 | 39.9 | 39.7 | 61 |
| | Avg artery width (mm) | | 6.2 | 6.1 | 6.2 | 6.1 |
| | Avg bandage length (yards) | | | 4.2 | 4.0 | 5.5 |
| | Avg 45 sec blood loss (g) | | 608 | 627 | 735 | |
| | Avg ooze blood loss (g)* | | | | 215 | |
| | Avg ooze blood loss (g)** | | | | 1176 | |
| | MAP | | | | 36 | |

\* Data from swine that had 3 hr survival
\*\* Data from all swine
Data not collected
Samples not tested in model

| Prototypes | | | | | |
|---|---|---|---|---|---|
| 120808 | 08-XL-045 | 08-XL-012 | 08-XL-013 | 08-XL-015 | 08-XL-039 |
| J & J Kling roll | J & J Kling roll | Shaoxing HengSheng | Shaoxing HengSheng | Shaoxing HengSheng | Nat'l. Wiper |
| 30/70 | 30/70 | 50/50 | 0/100 | 70/30 | Unknown |
| 55 | 55 | 55 | 60 | 55 | Unknown |
| aperture, creped | aperture, creped | butterfly, no ap | sm aperture | sm aperture | tissue sm ap |
| 63 | 94 | 276 | 201 | 268 | 58 |
| 29 | 59 | 34 | 14 | 29 | 7 |
| 1827 | 5546 | 9480 | 2866 | 7843 | 406 |
| 1 | 1 | 15 | 1 | 1 | 1 |
| 0.22 (0.03) | 0.23 (0.07) | 0.1 (0.06) | 0.2 (0.05) | 0.13 (0.03) | 0.70 (0.27) |
| 10% | 10% | 0 | 0 | 0 | 0 |
| 21.9 | 17.6 | 18.3 | 20.0 | 20.4 | 25.8 |
| - | - | + | + | + | - |
| 128 (89) | 26 (12) | >180 | 280 (147) | 109 (66) | 2 (1) |
| 70.1 | 70.4 | 43.6 | | | 80.6 |
| 3.4 | 3.1 | 7.3 | | | -6.3 |
| 10.2 (1.0) | 13.4 (7.4) | 5.3 (0.2) | 1.1 (0.7) | 8.1 (0.2) | 6.6 (0.6) |
| 3.12 | 3.11 | 4.75 | 1.34 | 4.98 | 0.89 |
| 1.8 | 2.1 | 1.44 | 1.06 | 1.62 | 0.93 |
| 6.81 | 9.06 | 7.63 | 7.25 | 7.73 | 9.12 |
| 0.75 | 0.69 | 0.25 | 0.88 | 0.57 | 0.91 |
| 13.42% | 9.47% | 3.31% | 15.25% | 8.8% | 9.59% |
| 0.28 | 0.26 | 0.15 | 0.34 | 0.27 | 0.35 |
| 5.36% | 3.18% | 1.94% | 5.62% | 3.90% | 4.05% |
| 11/16 | 13/18 | 15/16 | 11/17 | 10/16 | 12.17 |
| 4.25 | 4.06 | 2.00 | 4.37 | 4.22 | 3.77 |
| RD193 | RD193 | RD193 | | | |
| 7/8 | 5/8 | 1/4 | | | |
| 88% | 63% | 25% | | | |
| 5/8 | 2/8 | 0/4 | | | |
| 63% | 25% | 0% | | | |
| 6/8 | 4/8 | 0/4 | | | |
| 75.0% | 50.0% | 0.0% | | | |
| 7/11 | 5/14 | 1/8 | | | |
| 64% | 36% | 13% | | | |
| 41.1 | 39.5 | 41.9 | | | |
| 6.1 | 6.3 | 6.5 | | | |
| 3.9 | 3.9 | 4.8 | | | |
| 676 | 597 | 756 | | | |
| 36 | 211 | 309 | | | |
| 434 | 1335 | 3002 | | | |
| 33 | 31 | 26 | | | |

\* Data from swine that had 3 hr. survival
\*\* Data from all swine
Data not collected
Samples not tested in model

| Prototype ID | Description | Carrier Strip Raw Material | | Soaking Technique | Removal Technique | Drying | n | Processing Outputs | | |
|---|---|---|---|---|---|---|---|---|---|---|
| Lot # | | Base | Creping | | | | | mean wet wt. g (sd) | mean dry wt. g (sd) | mean dry length, in (sd) |
| RD0409035 | OMLC (120808) process with 40/60 | 40/60 | 25% comp. 260°F | Soaked/agitated overnight | Squeegee | 50°F Overnight | 21 | 77.4 (12.2) | 19.2 (1.3) | 144 |
| RD0409034-1 | HemCon scale-up process v1 with 40/60 | 40/60 | 25% comp. 260°F | No soak | Rolling member | 50°F Overnight | 20 | 85.5 (4.5) | 20.3 (1.1) | 144 |
| RD0409034-2 | HemCon scale-up process v2 with 40/60 | 40/60 | 25% comp. 260°F | 2 hr. soak | Rolling member | 50°F Overnight | 15 | 93.4 (3.7) | 19.7 (0.7) | 144 |
| RD0409034-3 | HemCon scale-up process v3 with 40/60 | 40/60 | 25% comp. 260°F | No soak | Rolling member | 50°F Overnight | 15 | 98.8 (3.9) | 24.5 (0.8) | 144 |
| RD0409034-4 | HemCon scale-up process v1 with 20/80 | 20/80 | 25% comp. 250°F | No soak | Rolling member | 50°F Overnight | 3 | 93.9 (5) | 25.6 (2.3) | 144 |
| 120808 | OMLC method produced by OMLC | J & J Kling roll | | Soaked/agitated overnight prior to liquid removal | Squeegee | 50°F Overnight | | 74.1 (7.5) | 13.4 (0.7) | 103 (3.8) |
| 08-XL-045 | HemCon method | J & J Kling roll | | Overnight "Hold" after rolling member | Rolling member | 50°F Overnight | | 71.8 (4.0) | 13.4 (0.6) | 79.1 (2.4) |
| 09-130-001 | OMLC method produced by HC | J & J Kling roll | | Soaked/agitated overnight prior to liquid removal | Squeegee | 50°F Overnight | | 73.8 (7.7) | 13.7 (0.8) | 108 (5) |

Fig. 27A(1)

| Fig. 27A |
|---|
| Fig. 27A(1) |
| Fig. 27A(2) |

| In Vitro Data | | | | | | | | | | | | |
|---|---|---|---|---|---|---|---|---|---|---|---|---|
| Density mean gsm | Absorption Capacity g/g | Wicking Rate mm/min MD | Wicking Rate mm/min CD | Single Drop Absorption Time to reach 5µl sessile | Permeability mean flow rate ml/sec (sd) | Gurley Stiffness MD (length) | Gurley Stiffness CD (width) | Gurley Stiffness Product | % Moisture | % Acid | Thickness mm | Liquid Absorption Time sec |
| 50.9 | 7.3 (0.5) | 2 | 2 | 180 | 0.2 (0.11) | 20.1 | 22.6 | 454.3 | 2.42 | 1.32 | 0.563 | 94 |
| 56.2 | 7.1 (1.3) | 1 | 2 | 180 | 0.24 (0.21) | 32.8 | 18.7 | 613.4 | 2.5 | 1.23 | 0.619 | 229 |
| 54.1 | 7.5 (0.7) | 2 | 2 | 182 | 0.19 (0.23) | 27.5 | 17.4 | 478.5 | 2.12 | 1.21 | / | / |
| 67.6 | 5.3 (0.4) | 1 | 2 | 180 | 0.40 (0.34) | 62.7 | 17.2 | 1078.4 | 2.42 | 1.42 | / | / |
| 62.9 | 4.9 (0.9) | 1 | 1 | 180 | 0.16 (0.06) | 41.5 | 11 | 456.5 | 2.11 | 1.08 | / | / |
| 55 | 10.2 (1.0) | 7 | 3 | 117 (55) | 0.22 (0.08) | 63 | 29 | 1827 | 3.12 | 1.8 | 0.757 | / |
| 67 | 10.4 (0.7) | 22 | 20 | 26 (12) | 0.23 (0.07) | 94 | 59 | 5546 | 3.11 | 2.1 | 0.923 | / |
| 45 | 10.6 (2.2) | 9 | 8 | 68 (46) | 0.12 (0.04) | 60 | 34 | 2040 | 2.68 | 1.9 | | |

Dressing Assembly Comprising a Chitosan Solution, a Binding Agent and a Carrier Strip Comprising 30% Rayon and 70% Polyester Dressing Assembly Comprising a Chitosan Solution and a Carrier Strip Comprising 30% Rayon and 70% Polyester

*Dressing Assembly Comprising a Chitosan Solution and a Carrier Strip Comprising 30% Rayon and 70% Polyester*

Dressing Assembly Comprising a Chitosan Solution and a Carrier Strip Comprising 50% Rayon and 50% Polyester

*Dressing Assembly Comprising a Chitosan Solution and a Carrier Strip Comprising 50% Rayon and 50% Polyester*

*Dressing Assembly Comprising a Chitosan Solution and a Polyester Carrier Strip*

*Dressing Assembly Comprising a Chitosan Solution and a Polyester Carrier Strip*

*Dressing Assembly Comprising a Chitosan Solution and a Carrier Strip Comprising 30% Rayon and 70% Polyester*

Dressing Assembly Comprising a Chitosan Solution and a Carrier Strip Comprising 30% Rayon and 70% Polyester Dressing Assembly Comprising a Chitosan Material

*Dressing Assembly Comprising a Chitosan Solution and a Carrier Strip Comprising 70% Rayon and 30% Polyester*

Uncoated Barrier Strip, Interfacing with Blood

Dressing Assembly Comprising a Chitosan Solution and a Carrier Strip Comprising 30% Rayon and 70% Polyester, Interfacing with Blood

120808

*Dressing Assembly Comprising a Chitosan Solution and a Carrier Strip Comprising 30% Rayon and 70% Polyester, Interfacing with Blood*

Dressing Assembly Comprising a Chitosan Solution and a Carrier Strip Comprising 30% Rayon and 70% Polyester, Interfacing with Blood

WOUND DRESSING DEVICES AND METHODS

RELATED APPLICATIONS

The present application claims priority to U.S. provisional application, Ser. No. 61/049,831, filed on 2 May 2008.

BACKGROUND OF THE INVENTION

The present invention is related to flexible wound dressings and more specifically to flexible wound dressings that have therapeutic qualities.

Controlling bleeding, fighting infection and improving wound healing are major medical issues. Methods to control bleeding and repairing wounds have existed for many years. Traditional surgical hemostatic techniques have included applying pressure, cauterizing, and suturing. Over the past 20 years, a number of hemostatic agents and tissue sealants have been developed and are currently used in various surgical disciplines. The hemostatic agents act to stop bleeding either mechanically or by augmenting the coagulation cascade, whereas tissue sealants are products that bind to and close defects in tissue. Currently there are five major classes of the hemostatic agents and tissue sealants for surgical use, including fibrin glue, bovine collagen and thrombin, cyanoacrylate, polyethylene glycol polymer, and albumin crosslinked with glutaraldehyde. These hemostatic agents are mainly composed of allogeneic or hetreallogeneic proteins.

Recently, chitosan based hemostatic dressings have been shown to control aggressive hemorrhages from severe external injuries. The chitosan dressing acts to control severe hemorrhagic bleeding by first sealing the wound site followed by promotion of local blood coagulation. An external form of this chitosan wound dressing was cleared by the Food and Drug Administration for external temporary control of severely bleeding wounds intended for emergency use.

However, in some applications, for example, a narrow entry wound, current chitosan and nonchitosan based wound dressing are not effective at providing hemostasis, fighting infection and/or promoting wound healing. Currently available dressings are often too stiff and too rigid to fit in a narrow space or they are too flexible and porous to efficiently promote hemostasis. Powder based hemostatic products also have limited effectiveness as they are difficult to apply to bleeding sites through narrow wound entries.

SUMMARY OF THE INVENTION

The present invention provides a wound dressing assembly that can be used to stanch, seal, or stabilize bleeding at a site of tissue injury, tissue trauma, or tissue access. The wound dressing assembly is flexible so that it can be adapted and used to fit in narrow and small wound sites, while still providing sufficient stiffness at small wound sites so that it can properly address the wound site, promote hemostasis, and also capable of properly fitting to the wound.

Generally the wound dressing assembly comprises a flexible carrier material that is impregnated with a non-mammalian material for control of severe bleeding. The preferred non-mammalian material is poly [β-(1→4)-2-amino-2-deoxy-D-glucopyranose] more commonly referred to as chitosan. The combination of the chitosan on the carrier strip provides a unique structure, wherein the chitosan material forms films and layers extending between individual fibers interstices that comprise the carrier strip, with the films being dispersed in a varied arrangement throughout the dressing assembly.

An advanced supple wound dressing assembly for control of severe, life-threatening bleeding should preferably have the following properties:
i) easily and quickly applied in one step after removal from package;
ii) rapid and strong blood clotting;
iii) at least a minimal level of tissue adhesion;
iv) strong internal cohesive properties;
v) rapid and strong wound sealing;
vi) resistant to dissolution under strong blood flow;
vii) able to be treated roughly without compromising efficacy;
viii) the dressing assembly must be flexible enough so that it can address narrow and oddly shaped wound sites, while having sufficient stiffness to allow for concentration of blood sells throughout the dressing assembly when being used.

Other features and advantages of the invention shall be apparent based upon the accompanying description, drawings, and claims.

BRIEF DESCRIPTION OF THE DRAWINGS

FIG. 1A is a perspective view of a prior art wound dressing assembly, where seepage from the wound is shown spreading outwardly from the wound dressing.

FIG. 1B is a perspective view of another prior art dressing assembly, wherein the dressing is not sufficiently flexible to properly cover the wound.

FIG. 2 is a perspective view, of an absorbable wound dressing assembly in accordance with the present invention.

FIG. 3 is a pictorial depiction of a dry wound dressing assembly according to the present invention, demonstrating a chitosan material being attached to a dressing matrix.

FIG. 4 is a pictorial depiction of the wound dressing assembly shown in FIG. 3, demonstrating the assembly absorbing fluids, thereby causing the chitosan materials in the assembly to allow the individual fluid cells to coagulate on the chitosan material.

FIG. 27 provides a table comparing qualities of various wound dressing assemblies developed according to the present invention, as well as comparing the wound dressing assemblies to prior art dressing assemblies.

FIG. 27A provides another table comparing qualities various wound dressing assemblies developed according to the present invention, as well as comparing the wound dressing assemblies to prior art dressing assemblies.

DESCRIPTION OF THE PREFERRED EMBODIMENT

Figure 5:
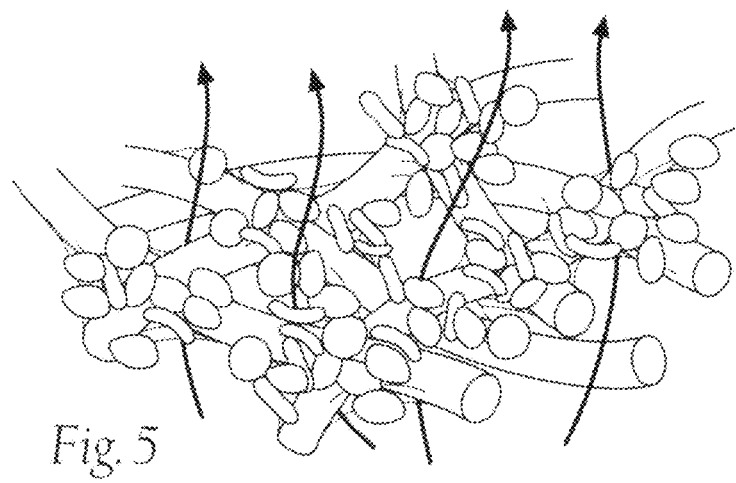
FIG. 5 is a three-dimensional depiction of the wound dressing assembly of FIG. 4, demonstrating the arrangement of the dressing matrix fibers and the attached chitosan material, with the individual cells coagulating on within the dressing assembly.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

The application is generally organized as follows:
A. Overview of the Wound Dressing Assembly and Its Uses
B. Manufacture of the Wound Dressing Assembly
C. Physical Description of the Wound Dressing Assembly
  I. Preparation of A Chitosan Solution
  II. Description of the Absorbable Carrier
  III. Physical Characteristics
D. Results
E. Other Uses of the Wound Dressing Assembly

A. Overview of the Wound Dressing Assembly and Its Uses

FIGS. 1A-7B provide a general overview of a wound dressing assembly 20 according to the present invention, with the assembly 20 compared to structures of the prior art to demonstrate the improved physical adaptability of the present invention. An arm 10 having a wound site 12 is depicted in the Figures with different assemblies addressing the wound site 12.

FIG. 1A shows a prior art gauze style assembly 14 wrapped around the arm 10 to cover the wound 12. The assembly 14 is flexible (i.e., not stiff) so it is capable of being wrapped around the arm 10 so that the wound site 12 is tightly covered. Still, the assembly 14 is not capable of stanching the flow of blood from the wound site 12 as desired. The volume of blood that flows into the assembly 14 prior to coagulation exceeds the absorbance capacity of the assembly 14. Not being absorbed by the assembly 14, excess blood flows outward from the wound site and beyond the periphery of the assembly 14. Further, the assembly 14 is free of a hemostatic material that is desired to accelerate or otherwise promote hemostasis. For these reasons, the assembly 14 is not completely effective at treating the wound site 12.

FIG. 1B shows another prior art pad style assembly 16 being applied to the wound site 12. As demonstrated, the assembly 16 includes a hemostatic material that accelerates or otherwise promotes hemostasis, and is thereby capable of stanching the flow of blood at the wound site. Still, the assembly 16 is stiff (i.e., not flexible), and cannot be wrapped around the arm 10 to hold the assembly 16 in place. If the assembly 16 is to be held in place, outside pressure needs to be applied to the assembly 16. Furthermore, if the wound site 12 is small or narrow, the assembly 16 may be too rigid to properly address the wound site 12.

FIG. 2 shows a supple wound dressing assembly 20 that embodies features of the present invention. The supple dressing assembly 20 comprises a flexible carrier structure 22 made from of a blood-absorbable material. The supple dressing assembly further includes a biocompatible, hemostatic material 24, preferably a chitosan material 24, deposited within the interstices of the carrier structure 22.

A close-up representation of the arrangement of the supple wound dressing assembly 20 is demonstrated in FIGS. 3-5. FIG. 3 represents the supple wound dressing assembly 20 in a dry state before being applied to a wound. The individual fibers of the carrier strip 22 provide a supporting structure for the chitosan material 24, which forms various dispersed web-like structures between the individual fibers. When the carrier strip 22 is treated with the chitosan material 24, which will be described further, below, the chitosan material 24 will adhere to the individual fibers that make up the carrier strip 22, and, surprisingly, also will form thin layers or membranes of material interspersed between the various individual fibers 22. In FIG. 4, the dressing assembly 20 is shown absorbing a fluid, i.e. blood, with the membranes of chitosan material 24 formed between the individual fibers of the carrier strip 22 collecting the majority of the individual red blood cells.

Figure 19:
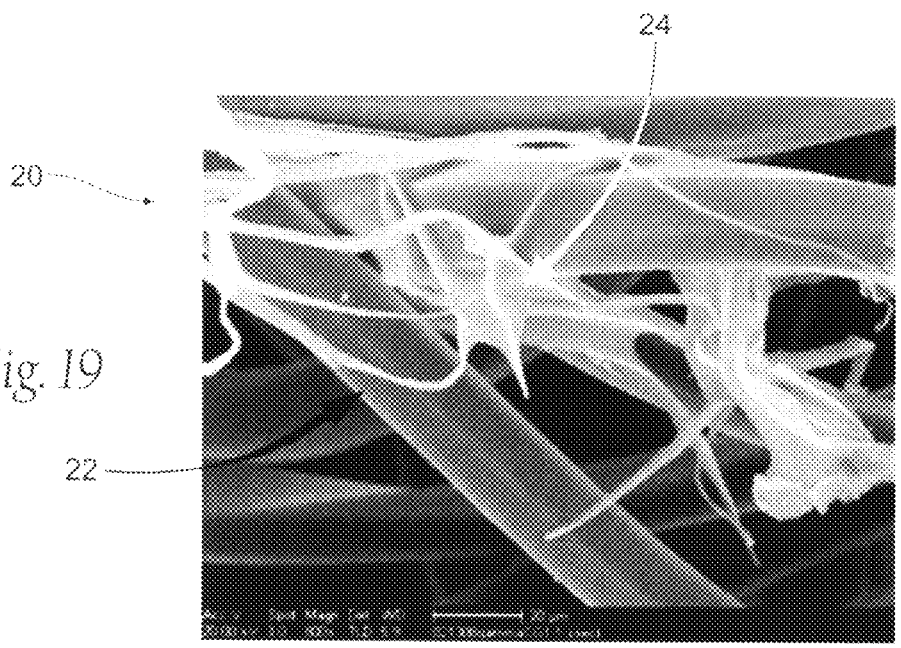
FIG. 19 showing a magnified view of the SEM image of FIG. 18.

While prior art and conventional wisdom would indicate that the chitosan material 24 would be coated onto the carrier strip 22 and would outwardly fill in the area around and between the individual carrier strip fibers in the carrier strip 22, the present invention provides an unexpected arrangement. That is, there are voids retained in the assembly 20, as shown in FIG. 19, with the chitosan material 24 also forming webs of material between various fibers and not necessarily coating those fibers. This lack of "solidification" of the saturated assembly 20 has a further advantage over prior dressing assemblies. The webs increase the surface area of the carrier strip, while still maintaining permeability. Not only does the arrangement let further blood seep into the dressing assembly 20, it also allows blood cells to aggregate and accumulate on the web-like areas of chitosan material 24 located in the dressing 20.

Figure 21:
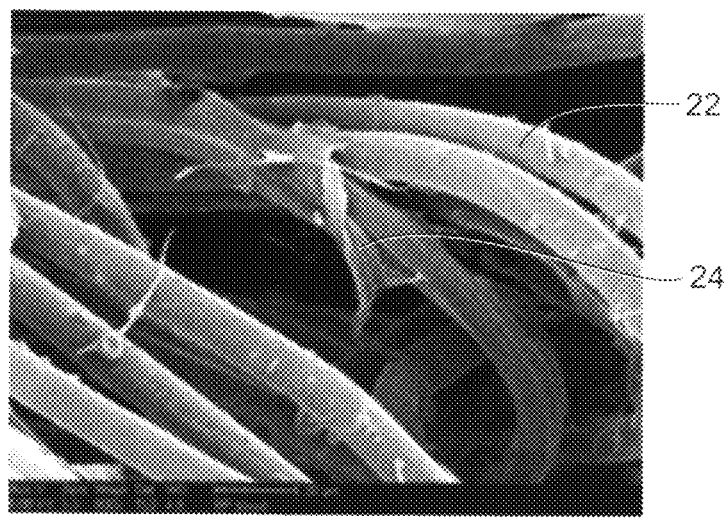
FIG. 21 provides a scanning electron micrograph (SEM) image of a dressing material developed according to the present invention prior to interacting with blood.
Figure 22:
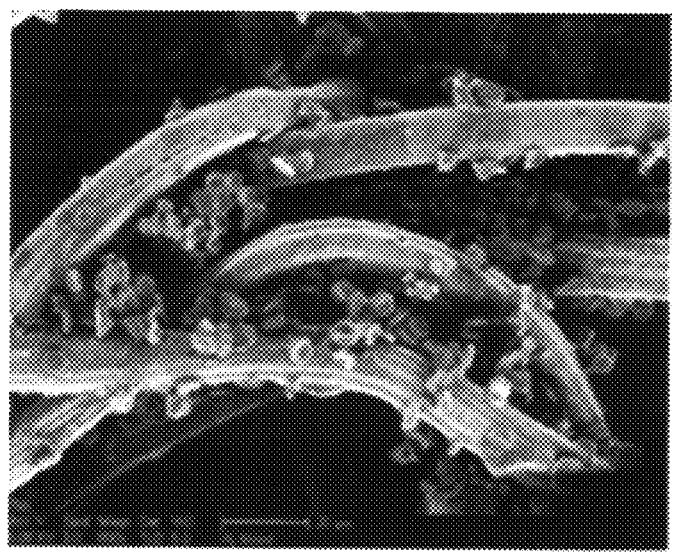
FIG. 22 provides a scanning electron micrograph (SEM) image of human blood interacting with a dressing material that does incorporates chitosan material, demonstrating marked blood cells accumulation and aggregation on the surface of assembled dressing.

The unique arrangement will be evidenced more distinctly with respect to magnified views of the dressings. (scanning electron micrograph (SEM) images) (FIGS. 18-22 and 28-43). For example, FIG. 21 provides a supple dressing assembly 20 prior to interaction with blood, while FIG. 22 shows the assembly of FIG. 21 after interaction with blood cells. The blood cells are shown accumulating on the various webs of chitosan material 24. These features will be discussed in further detail, below in Part C.

The dressing assembly 20 is characterized by a unique combination of suppleness or multi-dimensional flexibility, with a permeability and absorbance capacity to blood flow, that enhance the hemostatic capacity of the hemostatic material 24 to stanch blood flow at a wound site. As FIGS. 6, 7A, and 7B show, the dressing assembly 20 can be flexed, bent, folded, twisted, and even rolled upon itself before and during use, without creasing, cracking, fracturing, otherwise compromising the integrity and mechanical and/or therapeutic characteristics of the hemostatic material 24 it carries.

Figure 6:
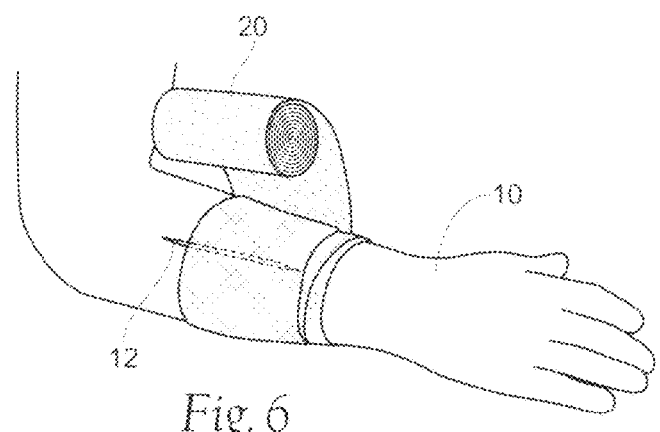
FIG. 6 is a perspective view of the wound dressing assembly shown in FIG. 2 being applied to a wound to stanch the bleeding of the wound.

As shown in FIG. 6, the supply dressing assembly 20 can be applied to the wound site 12 of the arm 10 in the manner of a conventional gauze wound dressing. The supply dressing assembly 20 is capable of being wrapped around the arm 10 to securely and independently apply pressure to the wound site. Further, as depicted in FIG. 7B, the flexible carrier structure 22 possesses the permeability and absorbance capacity to blood, so that blood exiting the wound site 12 stays localized within the confines of the assembly 20 and does not flow around and outside the periphery of the assembly 20. The blood is thereby brought into contact with the hemostatic material 24 that is carried within the interstices of the dressing assembly 20, to thereby stanch blood flow at the wound site 12.

The supple dressing assembly 20 provides a flexible structure 22 that can be adapted to a wide variety of wound shapes and areas, while the deposition of the hemostatic material 24 within the flexible structure 22 provides significant benefits in stanching and therapeutically treating a wound site 12.

Figure 7A:
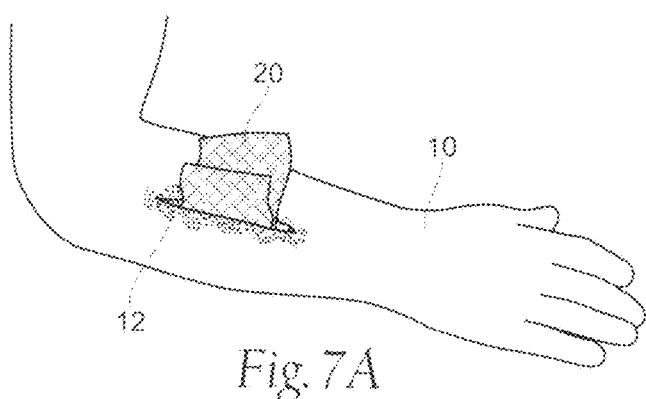
FIG. 7A shows the wound dressing assembly of FIGS. 2 and 6 being inserted into a narrow wound site to stanch the blood flow from the wound site and further promote hemostasis.
Figure 7B:
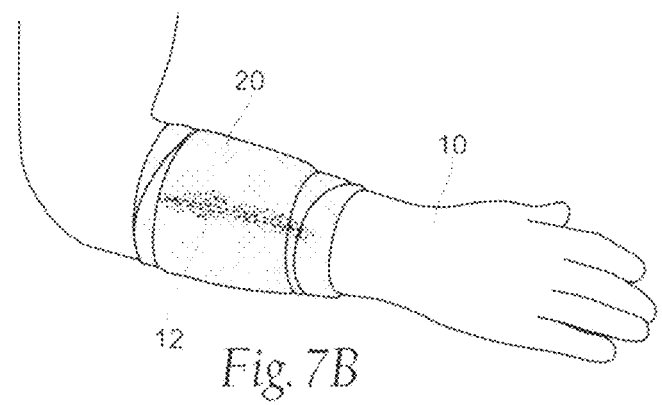
FIG. 7B shows the wound dressing assembly of FIGS. 2 and 6 administered on a wound and minimizing seepage of the wound outside of the wound dressing assembly.

FIG. 7A provides a further example of the flexibility and adaptability of the present invention. The dressing assembly 20 is shown not being wrapped around the arm 10 as depicted in FIG. 7B, but being inserted directly into the wound site 12. This is advantageous for deep, narrow, wounds and for quickly providing therapeutic qualities to the wound site 12.

The unique dressing assembly 20 can be characterized by a suppleness or multi-dimensional flexibility in terms of a Gurley stiffness value (in units of milligrams) (length×width) of not greater than about 10,000 (using a Gurley Stiffness Tester Model 4171D manufactured by Gurley Precision Instruments of Troy, N.Y., and Gurley ASTM D6125-97). It is believed that a dressing assembly 20 having a Gurley stiffness value (in units of milligrams) greater than about 10,000 does not possess the requisite suppleness or multi-dimensional flexibility to be flexed, bent, folded, twisted, and even rolled upon itself before and during use, and thereby comprising the integrity and/or mechanical and/or therapeutic characteristics of the hemostatic material 24 carried by assembly 20. However, the dressing assembly 20 should not have a Gurley stiffness value that is too low, as there will not be sufficient blood absorbance capacity within such an assembly. For example, a dressing assembly below a Gurley stiffness number below 200 is not preferable. The unique dressing assembly is characterized by a suppleness or multi-dimensional flexibility in terms of a Gurley stiffness value (in units of milligrams) between about 200-10,000, preferably between about 200-8000 and most desirably, between or about 500-6000.

The supple assembly 20 can also be characterized by a permeability to blood flow expressed in terms of a mean blood flow (in units of ml/sec). Blood flow is measured using the following procedure. A test piece of the dressing assembly that is 1" wide by the necessary length to achieve 0.8 g is inserted into a 10 cc plastic syringe with a diameter of 1 cm containing 3 cc of citrated whole bovine blood. Manual pressure is applied to the sample for 2 minutes. The syringe is then attached to a tubing line with 60 mmHg pressure of citrated whole bovine blood. The syringe is inverted and the rate at which blood flows through the dressing is recorded. It is believed that a dressing assembly 20 having a permeability that is less than about 0.1 ml/s, preferably not less than 0.15 ml/s, possesses too much resistance to blood flow that will lead to blood finding paths of lesser resistance outside the confines of the assembly, thereby shunting blood flow away the hemostatic material 24 carried within the interstices of the assembly 20. Similarly, a permeability that is too high will limit the effectiveness of a hemostatic material on a dressing assembly, as it will not provide sufficient impedance for the blood as it passes through the assembly. The unique dressing assembly 20 is characterized by a permeability to blood flow (in units of ml/sec) between about 0.1-0.5 ml/s and most desirably, between about 0.15-0.35 ml/s.

The supple assembly 20 can also be characterized by an absorbance capacity for blood in terms of a mean absorbance (in units of g/g). Total blood absorbency is measured according to the following procedure. A 2"×2" test piece of the dressing assembly is pre-weighed (W1) and placed in citrated whole blood for 2 minutes. The sample is removed from the blood and the excess blood is allowed to drip off for 30 seconds. The sample wetted with blood is weighed (W). The total blood absorbance capacity is calculated as (W1−W)/W.

Optimal absorbance capacity will be maintained in the present dressing assemblies 20 while possessing the qualities discussed above. It is believed that a dressing assembly 20 having an absorbance capacity that is less than about 5 g/g does not possess the requisite ability to absorb blood into the interstices of the assembly into contact with the hemostatic material 24. Like the lack of requisite permeability, the lack of requisite absorbance capacity will lead to blood flow outside the confines of the assembly, thereby shunting blood flow away the hemostatic material 24 carried within the interstices of the assembly 20. The unique dressing assembly 20 is characterized by an absorbance capacity for blood (in units of g/g) of not less that about 5 g/g, and most desirably, between about 5-15 g/g.

The single drop absorption time, which is generally characterized as the time for a single sessile 20 μl drop of blood to decrease in volume to a 5 μl drop of blood, for the dressing assembly 20 is in a preferred range, as well. The time, expressed in seconds, is preferably between 20-300 seconds, and more preferably between 60-240 seconds.

The supple assembly 20 is characterized by the unique properties discussed above. The described assembly provides unique permeability, absorbance, and stiffness qualities, thereby providing an assembly that has effective and advantageous qualities of both stiffer and flexible prior art assemblies. The qualities of the dressing fall within a range not previously realized with hemostatic dressings, wherein the dressing has the adaptability characteristics of prior art gauze-style dressings, while providing hemostasis similar to pad-type products.

B. Manufacture of the Wound Dressing Assembly

A desirable methodology for making the wound dressing assembly 20 will now be described. It should be realized, of course, that other methodologies can be used. Generally speaking, the methodology consists of providing a solution of chitosan material 24, applying the solution to a carrier strip 22, removing excess solution from the carrier strip 22, and drying the carrier strip 22 to form the supple dressing assembly 20.

Figure 8:
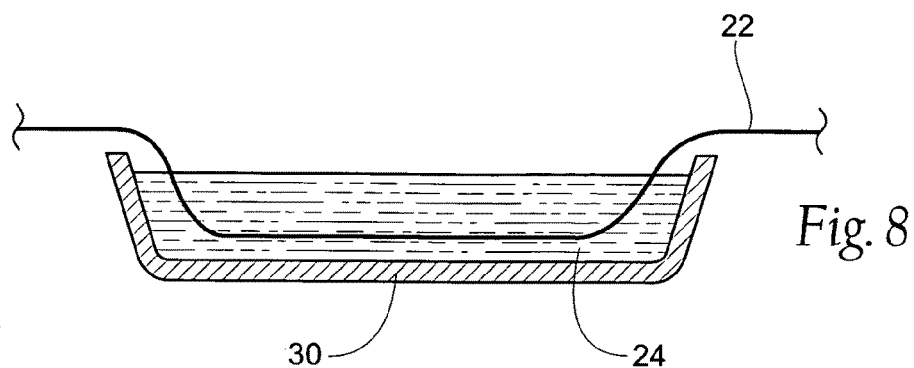
FIG. 8 is a schematic representation of a chitosan solution being applied to the carrier strip for the wound dressing assembly by soaking the carrier strip in the chitosan solution.
Figure 9:
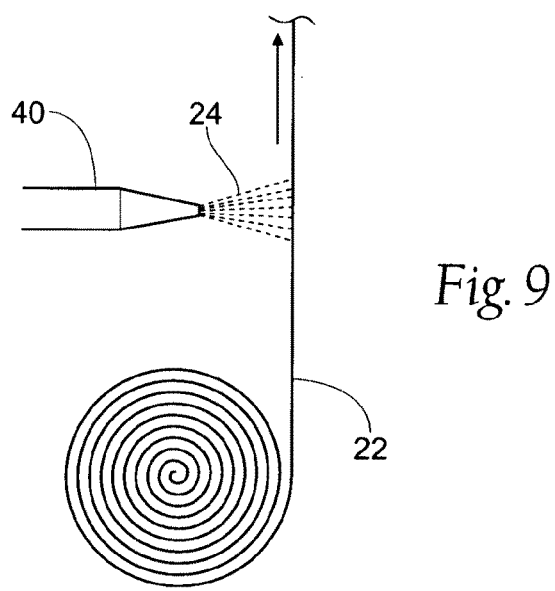
FIG. 9 is a schematic representation of a chitosan solution being applied to the carrier strip by spraying the carrier strip with the chitosan solution.
Figure 10:
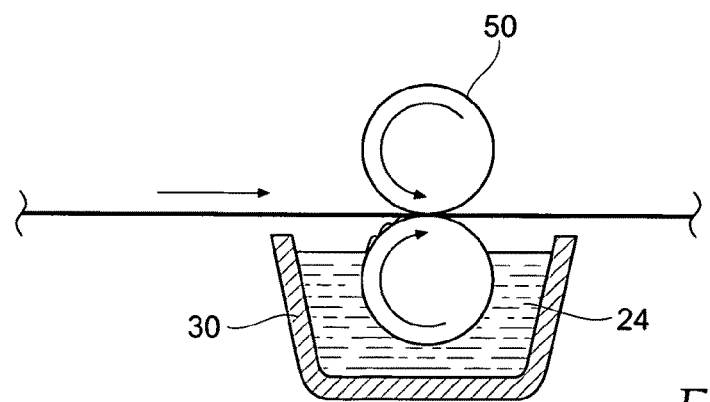
FIG. 10 is a schematic representation of a chitosan solution being applied to the carrier strip by passing the carrier strip through a set of rollers.
Figure 11:
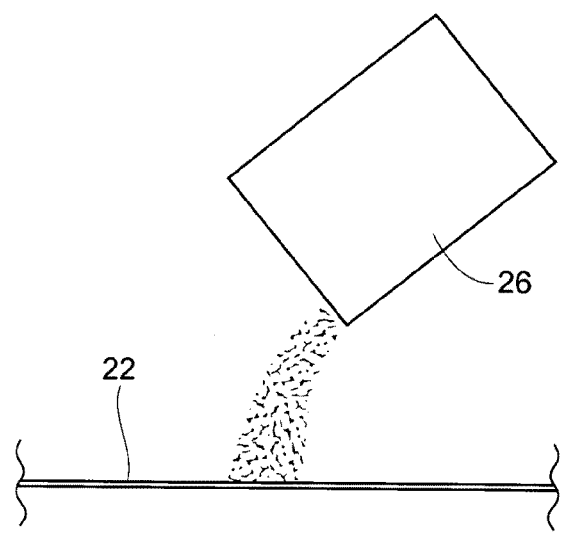
FIG. 11 is a schematic representation of a dry chitosan powder being added to the carrier strip for the wound dressing assembly, either with or without a liquid chitosan solution being applied to the carrier strip.

FIGS. 8-10 depict various methods that can be employed to apply the chitosan solution to the carrier strip 22. Generally speaking, the carrier strip 22 must be sufficiently wetted, either by directly placing the carrier strip 22 into the chitosan solution, or first submerging the carrier strip 22 into an aqueous solution, and then applying a chitosan material to the carrier strip. Wetting or soaking times are between 0-72 hours, with a typical soaking time being between 0-16 hours, with a more preferable soaking being between about 0-4 hours.

FIG. 8 provides a container 30 containing the chitosan solution 24. The carrier strip 22 will be submerged within the container 30, thereby absorbing the chitosan solution 24 onto the carrier strip 22.

FIG. 9 demonstrates the chitosan solution 24 being applied to the carrier strip 22 by way of a spraying device 40. An example of such a spraying device could be an electrospraying device.

FIG. 10 shows the carrier strip 22 being fed through a rolling member 50 to mechanically integrate the chitosan material into the carrier strip 22. The rolling member will be in contact with the container 30 containing the chitosan solution 24, thereby transferring the chitosan solution onto the carrier strip 22 as the passes through the rolling member 50.

Figure 12:
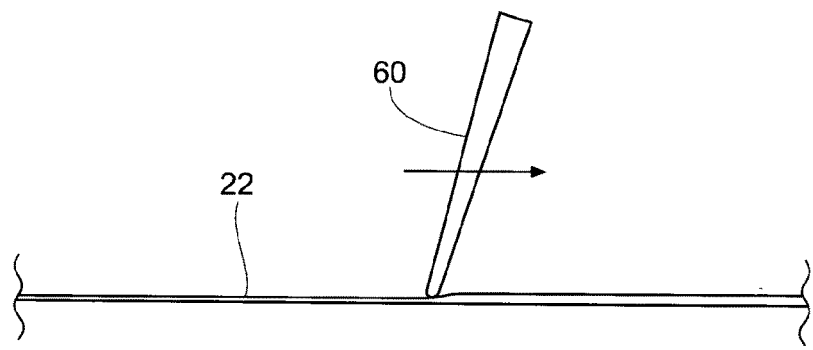
FIG. 12 is a schematic representation of excess liquid and/or chitosan powder being removed from a wound dressing matrix after the chitosan material has been applied to the wound dressing matrix.
Figure 13:
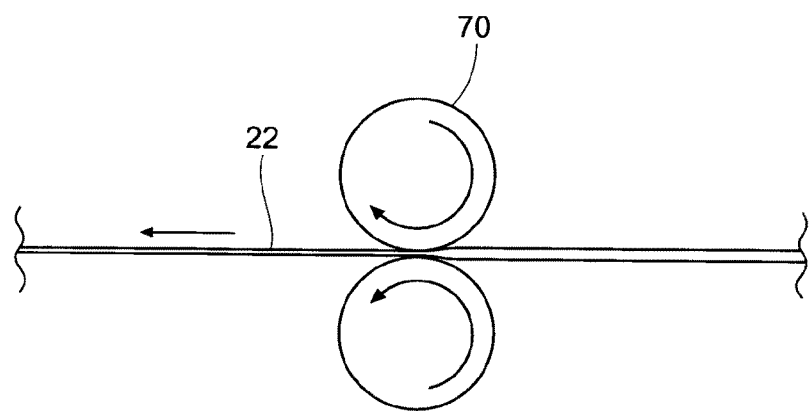
FIG. 13 is an alternate schematic representation of excess liquid and/or chitosan powder being removed from the carrier strip after the chitosan material has been administered to the carrier strip.

It should be understood that any process involving the addition of the chitosan solution 24 to the carrier strip 22 must be of a sufficient time so that the carrier strip 22 will thoroughly absorb the chitosan solution. In certain embodiments of the present invention, the chitosan solution 24 is effectively immediately absorbed into the carrier strip 22. It also should be noted that dry chitosan material could be applied directly to the carrier strip 22 after the carrier strip 22 has been wetted, i.e. after the carrier strip 22 absorbs the chitosan solution 24. As shown in FIG. 9, dry chitosan flake 26 can be coated on the wetted carrier strip 22. Once the chitosan solution 24 and/or chitosan 26 have been applied to the carrier strip 22, the excess solution 24 (and dry chitosan flake 26) will be removed from the carrier strip 22. FIGS. 12 and 13 demonstrate possible methods for removing excess chitosan solution 24 and/or chitosan flake 26 from the carrier strip 22. In FIG. 12, the carrier strip 22 is run past a squeegee 60, to remove excess material from the strip 22. The squeegee method adds an additional mechanical softening process, increases the surface area, and lengthens the fibers of the carrier strip that will improve the stiffness, permeability, and blood interaction characteristics of the dressing assembly.

In FIG. 13, the carrier strip 22 is run past a rolling member 70, thereby removing excess material from the carrier strip. Other devices, such as scrapers or trowels, may be used to remove excess material. Further, excess chitosan flake 26 may be removed from the strip by shaking the carrier strip 22 or blowing compressed air over the carrier strip 22. Preferably, a range of about 1-100 grams of chitosan solution is used per every gram of carrier strip 22 (dry weight), with a preferred range being from about 1-10 grams being used, and a more preferred range being from about 5-6 grams being used per one gram of dry carrier strip 22 material.

Referring further to the methods described in FIGS. 12 and 13, the various methods for removing excess solution can potentially alter the final characteristics of the supple dressing assembly 20. FIGS. 27 and 27A provides characteristics of various supple dressing assemblies 20. Particularly, the assemblies referred to in FIG. 27 as 100808, 120808 were prepared according to the method described with respect FIG. 12, and the dressing assembly referred to as 08-XL-045 was prepared according to the method described with respect to FIG. 13. For FIG. 27A, the methods are noted, with the "squeegee" removal technique referring to the method of FIG. 12 and the "rolling member" technique referring to the method of FIG. 13. Each of the carrier strips 22 for the three assemblies 20 had the same composition, and the same amount of chitosan material 24 was applied to the carrier strips 22. The results indicate that 100808, 120808, i.e. the assemblies 20 prepared according to the squeegee method, have a lower Gurley stiffness value than the assemblies 20 made without using the squeegee method.

Figure 14:
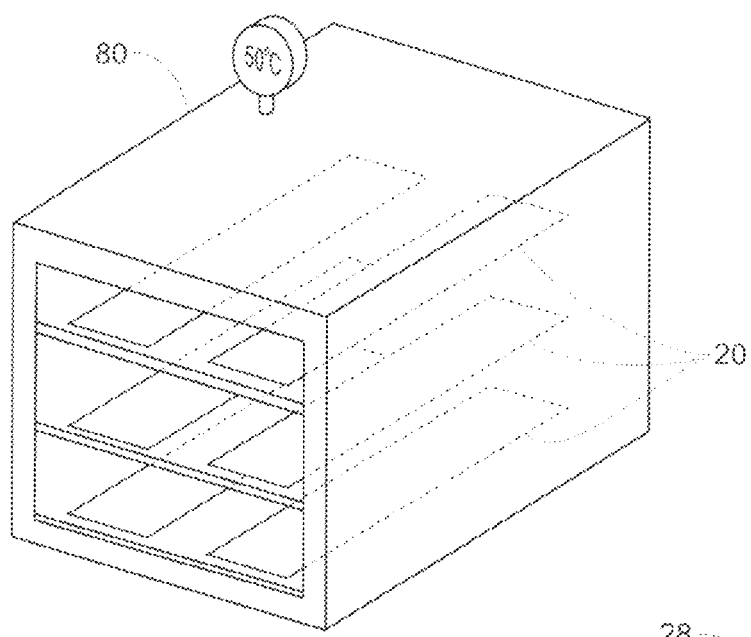
FIG. 14 depicts the wet wound dressing assembly comprising the chitosan material and the carrier strip being heated within the oven to dry the wound dressing assembly.

After removal of the excess solution 24 and/or chitosan flake 26, the carrier strip 22 will be placed within an oven 80 to heat and dry the carrier strip 22 to form the wound dressing assembly 20, as shown in FIG. 14. The oven 80 could be of various types of ovens or heaters, such as a conveyor oven, multideck oven, a microwave vacuum dryer, infrared dryer, or infrared heater. Depending on the type of oven used, and possibly the addition of an adhesive material 23 to the carrier strip 22, the drying time is preferably between about 1-24 hours, more preferably between about 12-24 hours, with overnight drying generally being standard procedure. Similarly, the drying temperature normally can be between 22°-100° C., more preferably between 40°-90° C. and more preferably between 50°-70° C.

Figure 15:
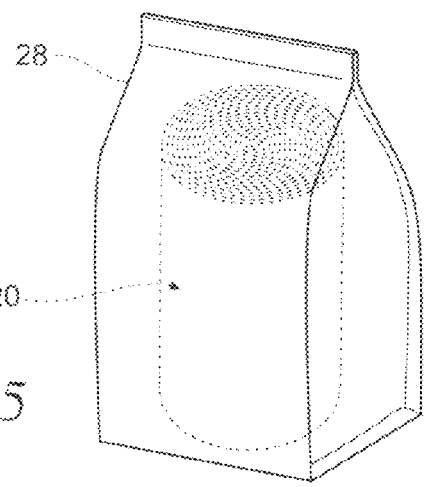
FIG. 15 shows the dried wound dressing assembly being stored within a pouch until the wound dressing assembly is to be used.

After drying is complete, the wound dressing assembly 20 can be subsequently packaged in a pouch 28 as shown in FIG. 15, which is desirably purged with an inert gas such as either argon or nitrogen gas, evacuated and heat sealed. The pouch 28 acts to maintain interior contents sterility over an extend time (at least 24 months) and also provides a very high barrier to moisture and atmospheric gas infiltration over the same period.

After pouching, the processed supple wound dressing assembly 20 is desirably subjected to a sterilization step. The wound dressing pad assembly 20 can be sterilized by a number of methods. For example, a preferred method is by irradiation, such as by gamma irradiation, which can further enhance the blood dissolution resistance, the tensile properties and the adhesion properties of the wound dressing. The irradiation can be conducted at a level of at least about 5 kGy, more preferably a least about 10 kGy, and most preferably at least about 25 kGy.

Figure 16:
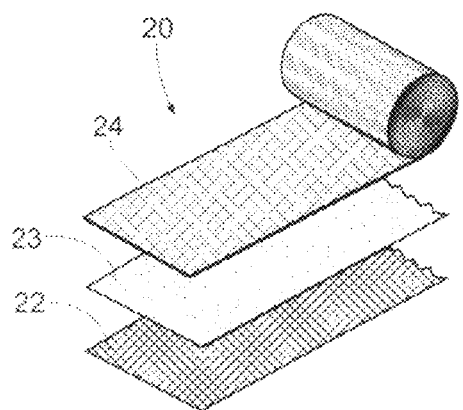
FIG. 16 is a perspective, exploded view of an alternate wound dressing assembly in accordance with present invention, with the dressing assembly further comprising a layer of adhesive material.

In an alternative step, an adhesive material 23 may be used to bind the carrier strip 22 with the chitosan material 24, which is shown in FIG. 16. Preferably, the adhesive material 23 would be added to the carrier strip 23 prior to addition of the chitosan material 24. Examples of adhesive materials could be lactic acid or polyacrylic acid (PAA). Typically, one is looking for ability to uniformly and robustly apply a final coat layer as efficiently as possible, as to enhance mating of base and top layer, i.e. the carrier strip 22 and the biocompatible material 24.

The following two examples demonstrate general preparation methods for a wound dressing assembly according to the present invention. More detailed examples are described with respect to the table shown in FIG. 27 and will be discussed in further detail, below, in Section C.

Example 1

A cotton gauze (i.e. carrier strip 22) was soaked in 1% chitosan and 2% acetic acid solution (chitosan material 24) for 12 hours. The gauze was stirred dry in an oven at 50° C. for 24 hours. The dry gauze (i.e. the wound dressing assembly 20) was then rolled and packaged in a heat-sealable pouch. The package was sterilized using gamma irradiation. The wound dressing assembly 20 had a moisture content of 1.58±0.44%, with the residual volatile acid content ranging from between 1 to 3.5%.

Example 2

A cotton-made gauze (i.e. carrier strip 22) was soaked in 1% chitosan and 2% acetic acid solution (chitosan material 24) for 12 hours. A chitosan powder (26) pretreated with acetic was coated on the gauze. The chitosan powder had a particle size of between 200 to 400 mesh and emitted zero or near zero volatile organic compounds. The excess powder was removed from the gauze, and the gauze was dried in an oven at 50° C. for approximately 24 hours. The dry gauze (i.e. the wound dressing assembly 20) was then rolled and packaged in a heat-sealable pouch. The package was sterilized using gamma irradiation.

The resultant wound dressing assembly 20 is capable of stanching the flow of blood and other bodily fluids at a wound site, as shown and described above with respect to FIGS. 2-7B. The improved absorbency and efficacy of the wound dressing is further described and discussed in the following section that described the physical properties of the dressing assembly.

C. Physical Properties of the Wound Dressing Assembly

I. Biocompatible Material

The biocompatible material 24 of the wound dressing assembly 20 comprises a non-mammalian material, which is most preferably poly [β-(1→4)-2-amino-2-deoxy-D-glucopyranose, which is more commonly referred to as chitosan. The chitosan selected for the matrix preferably has a weight average molecular weight of at least about 100 kDa, and more preferably, of at least about 150 kDa. Most preferably, the chitosan has a weight average molecular weight of at least about 300 kDa.

The chitosan used to prepare the chitosan solution preferably has a fractional degree of deacetylation greater than 0.75 but less than 0.97. Most preferably the chitosan has a fractional degree of deacetylation greater than 0.85 but less than 0.95. Preferably the chitosan selected for processing into the matrix has a viscosity at 25° C. in a 2% (w/w) solution of 2% (w/w) acetic acid (AA) with spindle LVI at 30 rpm, which is about 100 centipoise to about 2000 centipoise. More preferably, the chitosan has viscosity at 25° C. in a 2% (w/w) solution of 2% (w/w) acetic acid (AA) with spindle LVI at 30 rpm, which is about 100 centipoise to about 1000 centipoise. Most preferably, the chitosan has viscosity at 25° C. in a 2% (w/w) solution of 2% (w/w) acetic acid (AA) with spindle LV1 at 30 rpm, which is about 100 centipoise to about 500 centipoise.

The chitosan solution is preferably prepared at 25° C. by addition of water to solid chitosan flake or powder and the solid dispersed in the liquid by agitation, stirring or shaking. On dispersion of the chitosan in the liquid, the acid component is added and mixed through the dispersion to cause dissolution of the chitosan solid. The rate of dissolution will depend on the temperature of the solution, the molecular weight of the chitosan and the level of agitation. Preferably the dissolution step is performed within a closed tank reactor with agitating blades or a closed rotating vessel. This ensures homogeneous dissolution of the chitosan and no opportunity for high viscosity residue to be trapped on the side of the vessel. Preferably the chitosan solution percentage (w/w) is greater than 0.5% chitosan and less than 4.0% chitosan. More preferably the chitosan solution percentage (w/w) is greater than 1% chitosan and less than 2.3% chitosan. Most preferably the chitosan solution percentage is greater than 1.0% chitosan and less than 2.0% chitosan. Preferably the acid used is acetic acid. Preferably the acetic acid is added to the solution to provide an acetic acid solution percentage (w/w) at more than 0.8% and less than 4.0%. More preferably the acetic acid is added to the solution to provide an acetic acid solution percentage (w/w) at more than 1.5% (w/w) and less than 2.5%.

An adhesive material may be added to the chitosan material, as well. The dressing assembly may be capable of forming an adhesive material in combination with blood flowing from said wound at a wound dressing-blood interface. Preferably, the adhesive material, when hydrated by interaction with the blood interface, preferably has a pH of not less than about 5.5 when the wound is sealed. More preferably, the adhesive material preferably has a pH of not more than about 6.5 when the wound is sealed. Most preferably, the adhesive material preferably has a pH of not more than about 7.5 when the wound is sealed. Preferably, the adhesive material comprises an acid selected from the group consisting of acetic acid, formic acid, lactic acid, ascorbic acid, hydrochloric acid, and citric acid.

The wound dressing of the present invention has at least a minimal degree of adhesion to the wound site. Prior art carrier strips generally display no degree of adhesion. Preferably, the degree of adhesion is between 1 and 40 kPa, and more preferably between about 10-40 kPa.

II. Description of the Absorbable Carrier Strip

The absorbable carrier strip 22 used in the present invention generally comprises a flexible material, such as a low-modular mesh, film, or weave, either of a synthetic or naturally occurring polymer. The strip 22 preferably is defined by interconnected strands, filaments, or strips of material. The strands, filaments, or strips can be interconnected in any one or a combination of manners including, but not limited to, being woven into a gauze, intertwined, integrally-formed, and the like. Preferably, the interconnection is such that the mesh can flex while substantially maintaining the dimensions of the openings defined thereby.

The material from which the absorbable carrier strip is fabricated may be a polymer (e.g., nylon, polyethylene, polypropylene, polyester, or the like), metal, fiberglass, or an organic substance (e.g., cotton, wool, silk, or the like). Commercial versions of acceptable blood absorbent strips are available as gauzes and bandages, such as Johnson & Johnson Nu Gauze All Purpose Dressings, Kling Rolls, and First Aid Gauze Pads, Kendall Kerlix and Kerlix Lite Gauze, and gauzes sold by such companies as Walgreens, Safeway and Rite Way, to name a few. Preferably, the carrier strip 22 may comprise a creped or butterfly material, with or without apertures.

The wound dressing has an available blood contacting surface area per base surface of said wound dressing of preferably at least about 100 cm$^2$ per cm$^2$, more preferably at least about 200 cm$^2$ per gram per cm$^2$, and most preferably at least about 300 cm$^2$ per gram per cm$^2$. The available mass of chitosan biomaterial per wound surface area is preferably at least about 0.02 g/cm$^2$, more preferably at least about 0.04 g/cm$^2$, and most preferably at least about 0.06 g/cm$^2$ Furthermore, the wound dressing has a mean rate of dissolution per base surface area of said wound dressing when adhered to said wound site, at a temperature of about 37° C., of preferably not more than about 0.008 grams per minute per cm$^2$, more preferably not more than about 0.005 grams per minute per cm$^2$, and most preferably not more than about 0.002 grams per minute per cm$^2$.

The wound dressing assembly 20 provides an improved flexible dressing that can be adapted for use on or at wound sites of varying sizes and degrees. The dressing assembly 20 is easily wrapped around an injured body part and also provides the necessary absorbency required for preventing blood and other bodily fluids from flowing outwardly from the wound site. This is accomplished while delivering a therapeutic agent to a wound site by way of the wound dressing assembly 20. The following discussion of the interaction of the carrier strip 22 and the chitosan material 24 will further demonstrate the advantages of the present dressing assembly.

Figure 17:
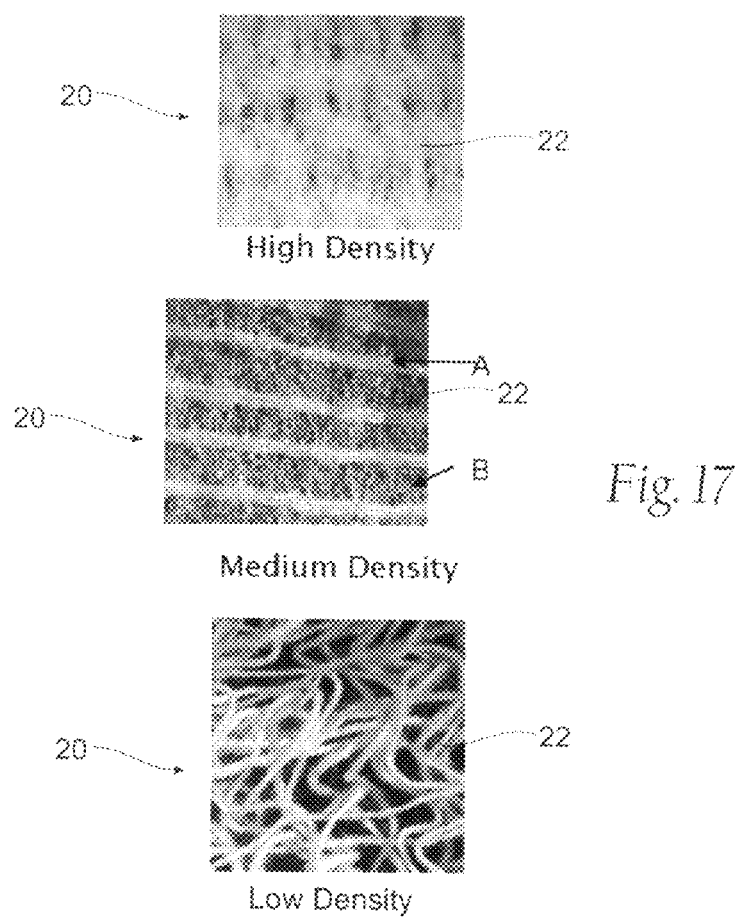
FIG. 17 provides scanning electron micrograph (SEM) images (5× resolution) of wound dressing assemblies according to the present invention, with the images demonstrating wound dressing assemblies having various densities.

FIG. 17 depicts various wound dressing assemblies 20 having various degrees of density for the carrier strip 22. The carrier strip is shown underneath the view of a scanning electron micrograph (SEM), wherein the image is magnified five times from normal. Any of the shown densities provide capable carrier strips 22. However, it has been determined that the density of the material should not be too low, which would not provide the necessary absorbency required, nor should the material be too dense, which would prevent absorbency altogether and may be too stiff of a material, as well. Preferable densities are dependent on the type of material that comprises the carrier strips 22, as well. For example, carrier strips made out of cotton gauze tend to show the greatest hemostatic efficiency when the density of the gauze is a medium density, while a nonwoven rayon/polyester blend material that formed the carrier strip would be preferably a high density to best promote hemostatic efficiency. Preferably the density range is between 20 and 200 g/m$^2$, and more preferably between 50 and 75 g/m$^2$.

An example of a suitable material is a combination of rayon and polyester in approximately 1:4-3:4 ratio with an average density of 62.2±2.2 g/m$^2$. mesh density with a special nonwoven textile technique. The material was tested, and the results are listed below in Table 1.

TABLE 1

| Characteristics of Carrier Strip Comprising Rayon and Polyester Materials | |
|---|---|
| Characteristics | Results (Avg.) |
| Generic Fiber content | 64% Polyester and 36% rayon |
| Weight (g/m$^2$) | 62.23 ± 2.24 |
| Thickness (mm) | 0.962 ± 0.046 |
| Stiffness (µjoules/m) | 1128.6 ± 150.4 |
| Air permeability (m3/m2/min) | 155.3 ± 5.8 |
| Tensile strength (µjoules/m) | Machine direction (MD): 66.4 ± 3.8 Cross direction (CD): 33.0 ± 4.7 |
| Elongation (%) | MD: 144 ± 12 CD: 219 ± 4 |
| Tearing strength (N) | CD: 6.43 ± 0.78 |
| Bursting Strength (kPa) | 138.3 ± 9.8 |
| Pilling resistance (visual rating) | 1 |
| Liquid absorbency time (sec) | 4.9 ± 0.3 |
| Liquid wicking rate | N/A |
| Demand absorbance capacity (g/g) | 3.54 ± 0.75 |
| Maximum absorption rate (g/g/sec) | 0.034 ± 0.015 |

III. Physical Properties of the Supple Dressing Assembly

FIGS. 27 and 27A provides a further comparison between supple wound dressing assemblies 20 of the present invention, along with a comparison to other prior art dressing assemblies. FIG. 27A demonstrates various wound dressing assemblies 20 encompassing preferred commercial embodiments. Reference to the Prototypes RD049034-(1-4) provide dressing assemblies 20 that have been produced with the carrier strip 22 material comprising about 40% polyester and about 60% rayon (i.e., 40/60 material). The strips 22 were general soaked in the chitosan solution 24 in a minimal time, 0-2 hours, with the assemblies being fed through the rolling members 50 (FIG. 13) and dried overnight. The resultant assemblies 20 are shown to be relatively pliable with a Gurley Stiffness value below about 1100, while still retaining the absorption and permeability qualities described and discussed above.

Along with the carrier strip 22, the chitosan material 24 also defines an absorbable material. The combination of the absorbable carrier strip 22 and the absorbable chitosan material 24 provides the improved overall properties of the wound dressing assembly. Generally speaking, the chitosan material 24 will bind to the individual fibers that make up the carrier strip 22, thereby forming webs and films between the various individual fibers of the carrier strip 22. The dressing assembly 20 further has open areas for blood to seep into the assembly, as well as areas for blood cells to coagulate. That is, the arrangement has open voids that allow fluids to move upwardly into the wound dressing assembly 20, as opposed to moving outwardly around a bandage or gauze, as shown in the prior art in FIG. 1A. Not only does this assist in absorbing blood and fluid, but also prevents the blood cells or cellular components from being disassociated from the plasma in the blood.

Figure 18:
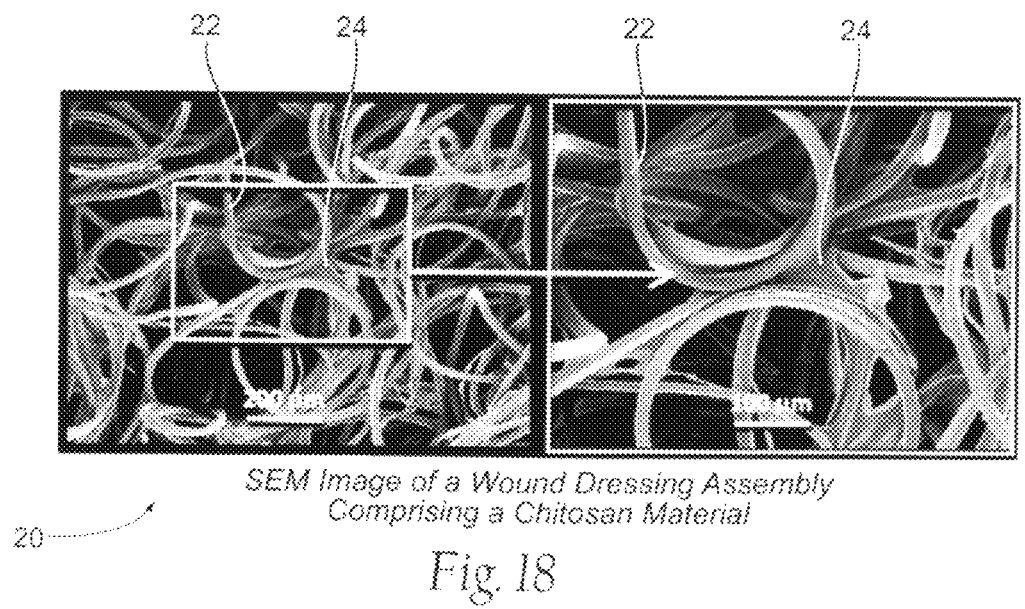
FIG. 18 shows an SEM image of a wound dressing assembly according to the present invention, wherein a cotton fiber material is coated with a therapeutic agent comprising 1% chitosan.

FIGS. 18 and 19 provide scanning electron micrograph (SEM) images of wound dressing assemblies 20 according to the present invention. The assemblies 20 are shown in a dry state, i.e. prior to being used. As is shown, the chitosan material 24 is bound onto and between the individual fibers of the carrier strip 22. The dressing assembly 20 still has large open areas located throughout the dressing assembly 20, which allows fluid to seep into the dressing assembly 20.

Figure 20:
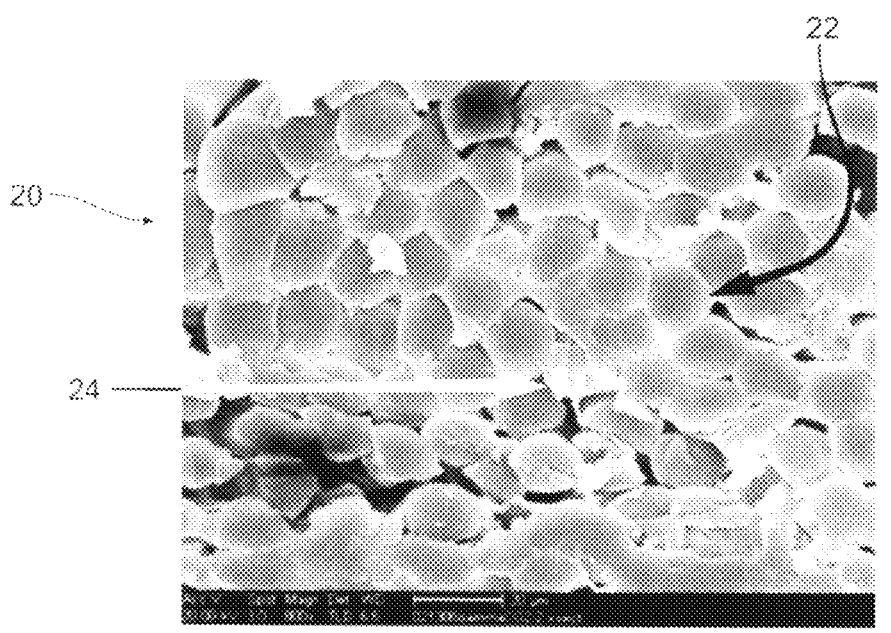
FIG. 20 shows an SEM image of a wound dressing assembly according to the present invention, wherein a cotton fiber material is coated with a therapeutic agent comprising 2% chitosan and the wound dressing assembly has expanded with the absorption of a fluid.

FIG. 20 provides a scanning electron micrograph (SEM) image of the wound dressing assembly 20 after a fluid has been absorbed into the assembly 20. The carrier strip 22 and the chitosan material 24 both have expanded with the fluid they have absorbed. However, there are still void areas within the dressing assembly 20, which allows fluid to move upwardly into the dressing assembly.

Figure 40:
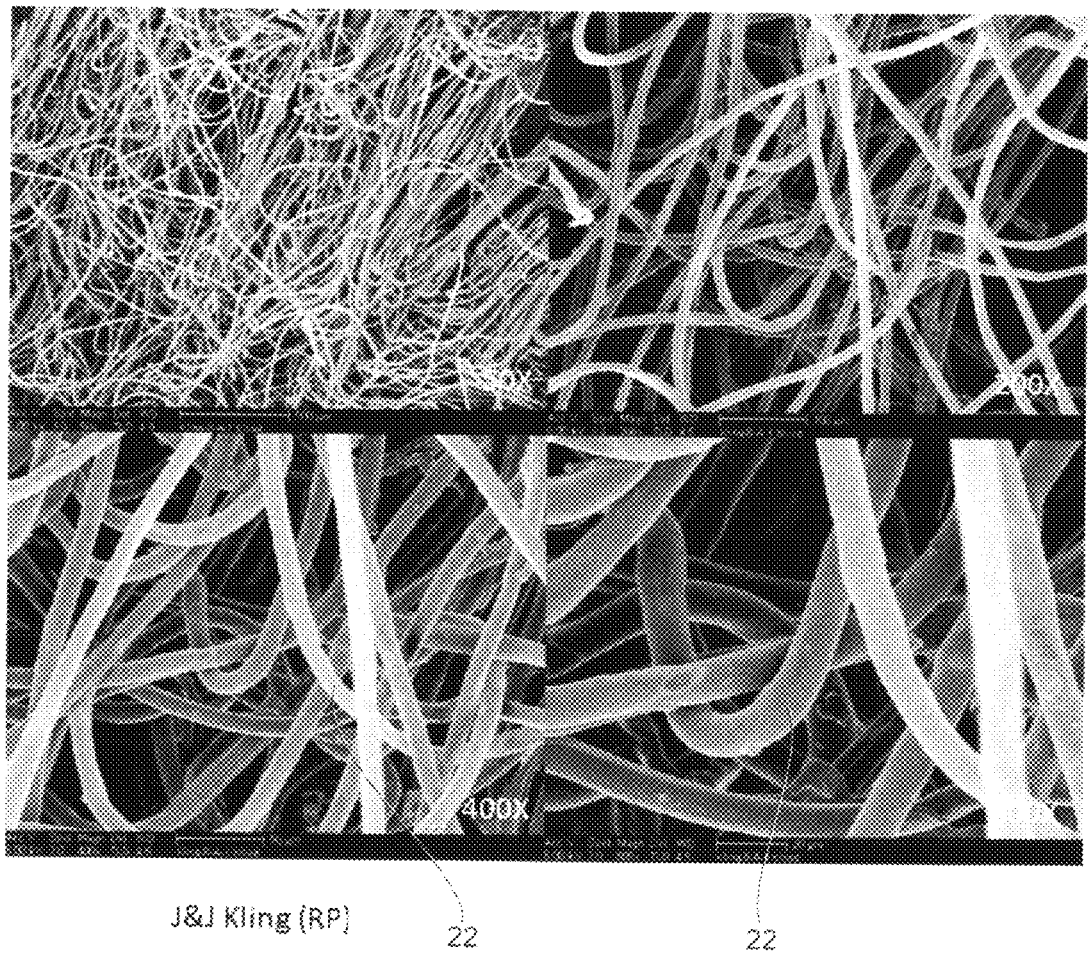
FIG. 40 is a scanning electron micrograph (SEM) image of a prior art dressing assembly interacting with blood.
Figure 41:
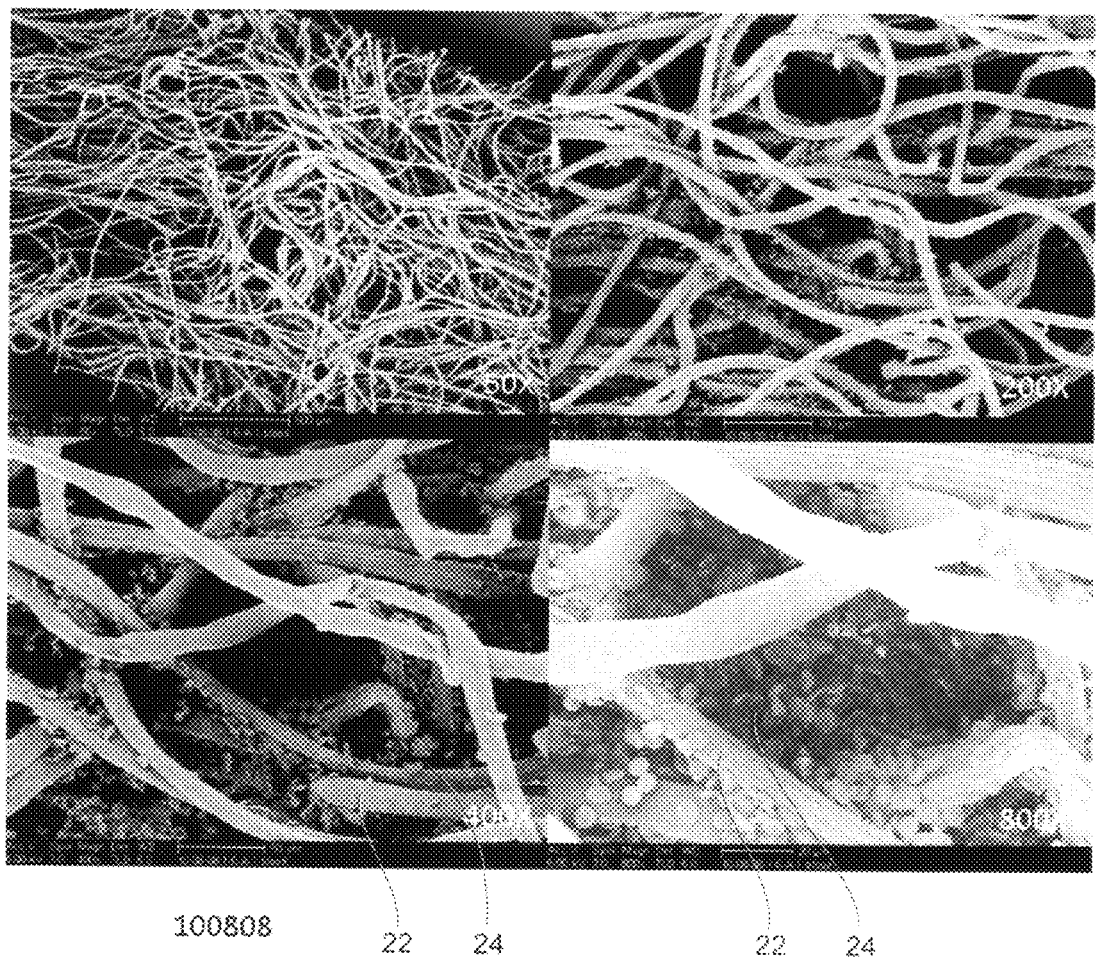
FIGS. 41-43 are various scanning electron micrograph (SEM) images of various wound dressing assemblies according to the present invention interacting with blood.
Figure 42:
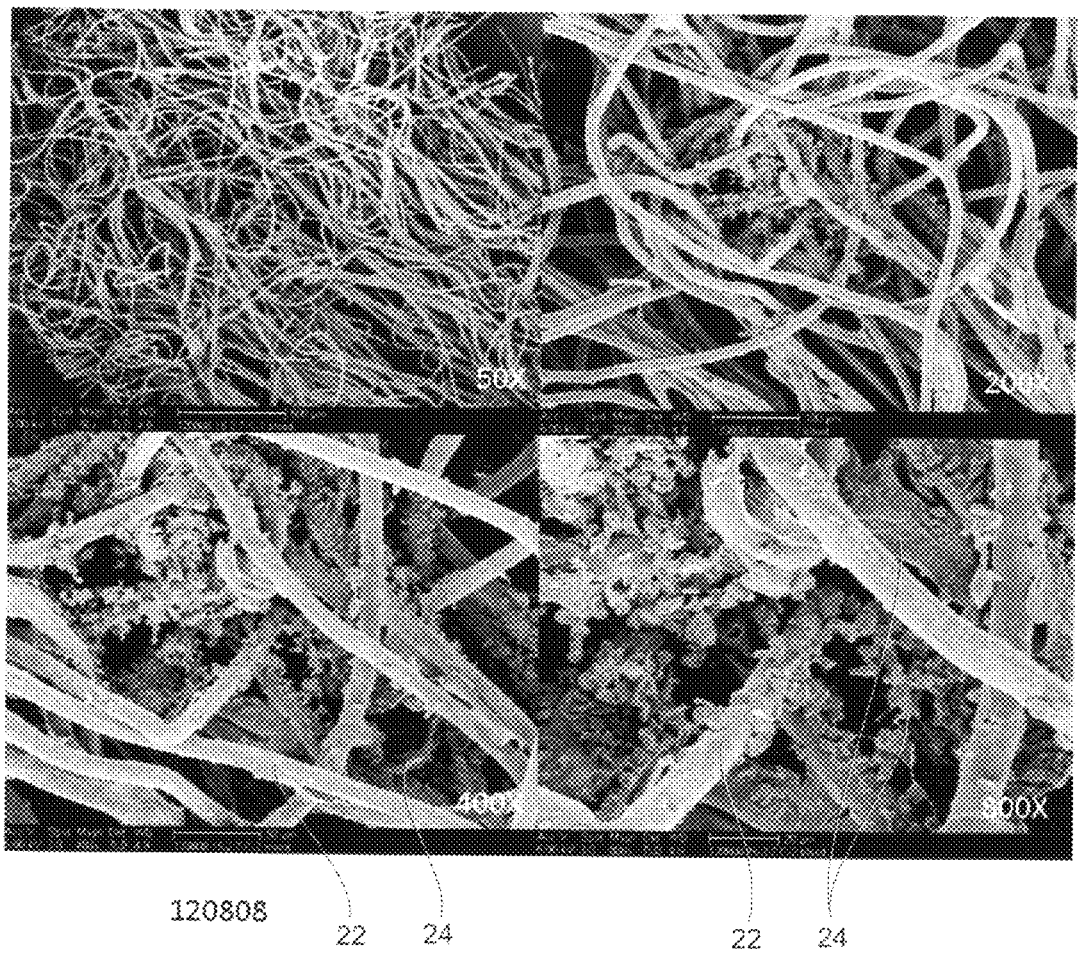
Figure 43:
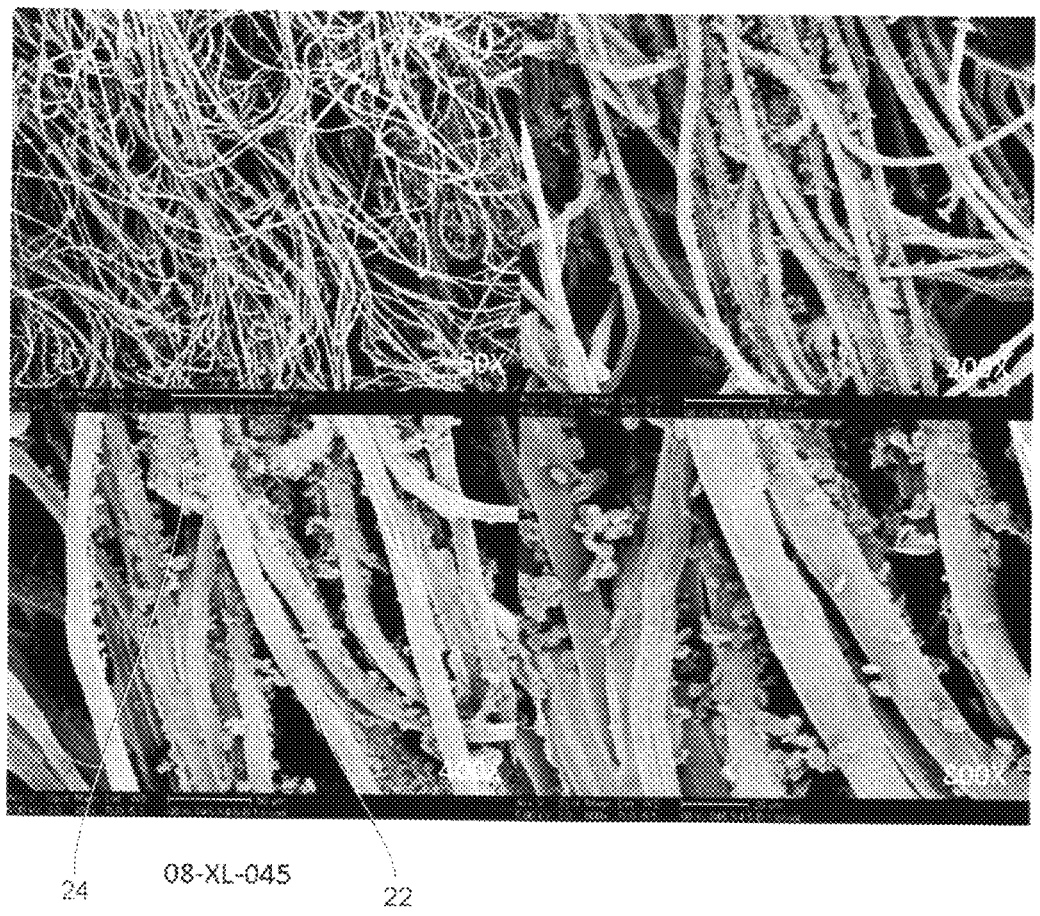

The assembly 20 of the present invention (FIG. 21) demonstrates marked blood cells accumulation and aggregation on the surface of the assembly 20 compared to the prior art dressings, which is shown in FIG. 40. In comparison, the cell count on the surface of the dressing assembly 20 is significantly higher $32,086 \pm 21390/mm^2$ than the cell count $4,456 \pm 2,674/mm^2$ of dressing of FIG. 40 that contains no chitosan material.

It has been further determined that total blood absorbance capacity (TBAC) of dressing assemblies 20 of the present invention is in a range of 0.5 to 12 g/g (gram blood absorbed/gram gauze), preferable in a range of 2-8 g/g, with the range of material prior to the addition of a chitosan material being in a range of 8 to 16 g/g, preferable in a range of 10-14 g/g.

While the general arrangement of the dressing assembly has been demonstrated, other variables may have an effect on the overall efficacy of the material by providing different adhesion or stiffness properties, or by altering the contact angle of the gauze.

Figure 23:
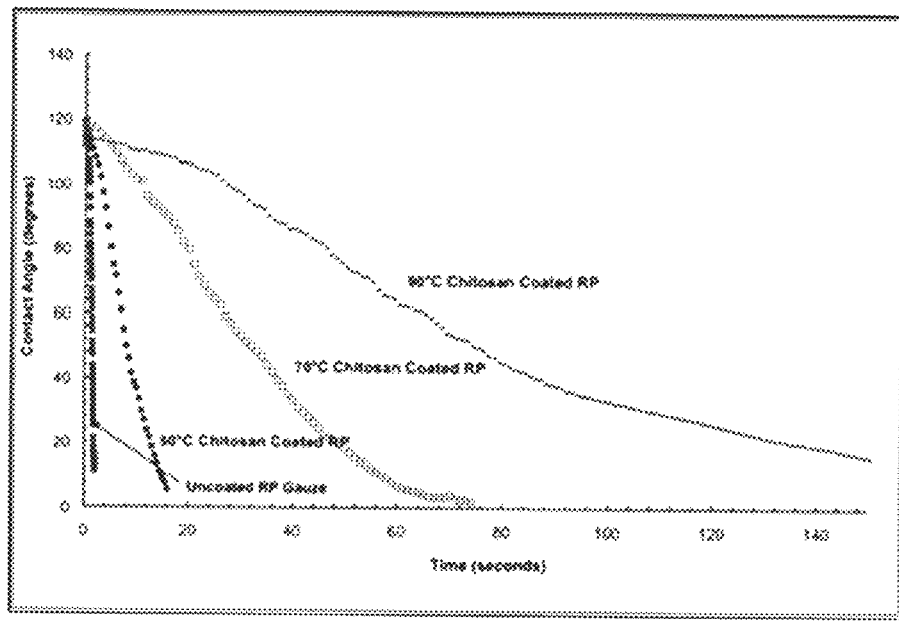
FIG. 23 is a graph showing the effect of drying temperatures on various wound dressing assemblies compared to the resultant contact angle for the various assemblies.

FIG. 23 is a graph comparing the contact angle of blood droplets on various wound dressing assemblies. The contact angle is the angle at which a specific fluid interface meets a solid surface and subsequently spreads out over the solid surface. That is, the contact angle measures how quickly the fluid dissipates into the solid surface. The tested wound dressing assemblies comprised a carrier strip comprising a blend of rayon and polyester (RP) that was impregnated with a chitosan material according to the present invention. Reference to an Uncoated RP Gauze is for a dressing assembly that has not been treated or impregnated with chitosan, i.e. a prior art dressing assembly. The dressing assemblies were compared at various temperatures, 50° C. for 24 hours, 70° C., and 90° C. For 4 hours. The contact angle was measured using an FTA200 contact angle instrument. A 20 μL blood droplet was placed on the surface of the various wound dressing assemblies and the change of the contact angle of the blood/wound dressing assembly was measured over time. The results indicate that the drying temperature of the wound dressing assemblies affects the assemblies by contact angles with different drying processes. Further, FIG. 23 demonstrates that the contact angle shows that the dressing assemblies of the present invention are improvements over the prior art dressing assemblies (the uncoated RP gauze) by their ability to provide a more utile, efficacious, flow rate of blood into the wound dressing.

Figure 24:
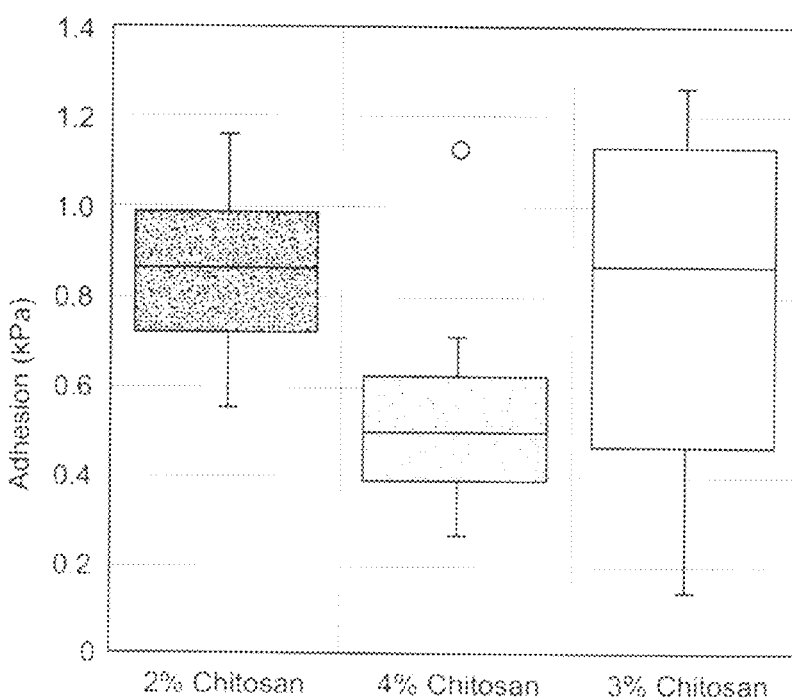
FIG. 24 is a graph comparing the adhesion strength for wound dressing assemblies with various amounts of chitosan material.

FIG. 24 is graph comparing the adhesion properties of wound dressing assemblies of the present invention having various amounts of chitosan material applied to the dressing assemblies (2%, 3%, 4%). The adhesion was performed using an Instron instrument with a 10N load cell. Bovine blood (0.25 ml) was placed on a test piece of each of the dressing assemblies. A 0.4 inch PVC probe was then held in contact with the test pieces at 15 kPa for seconds and then removed. The results indicate that each of the various amounts of chitosan used do have acceptable adhesion properties. As discussed, above, the dressing assemblies will have at least a minimal degree of adhesion, preferably between about 10-40 kPa.

Figure 25:
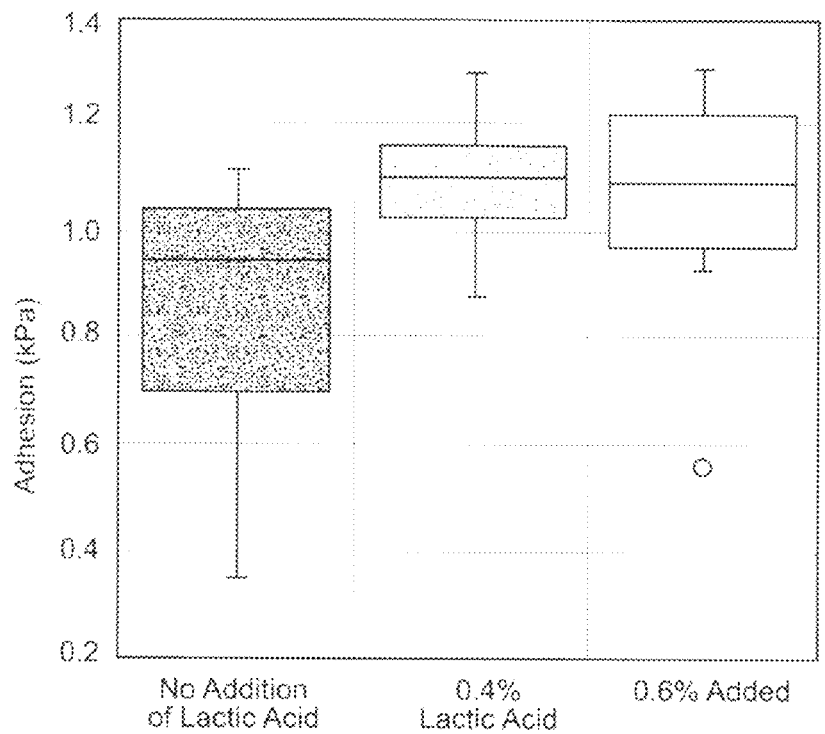
FIG. 25 is a graph comparing the adhesion strength of wound dressing assemblies with various amounts of lactic acid added to the dressing assemblies.

FIG. 25 is a further graph comparing wound dressing assemblies of the present invention. The dressing assemblies, which each comprised a 2% chitosan material, were subjected to various amounts of lactic acid (0%, 0.4%, and 0.6%). The adhesion test was the same as what was carried out with respect to FIG. 21. The results indicated that addition of non-volatile acid does not significantly enhance the adhesion property of the dressing assemblies.

Figure 26:
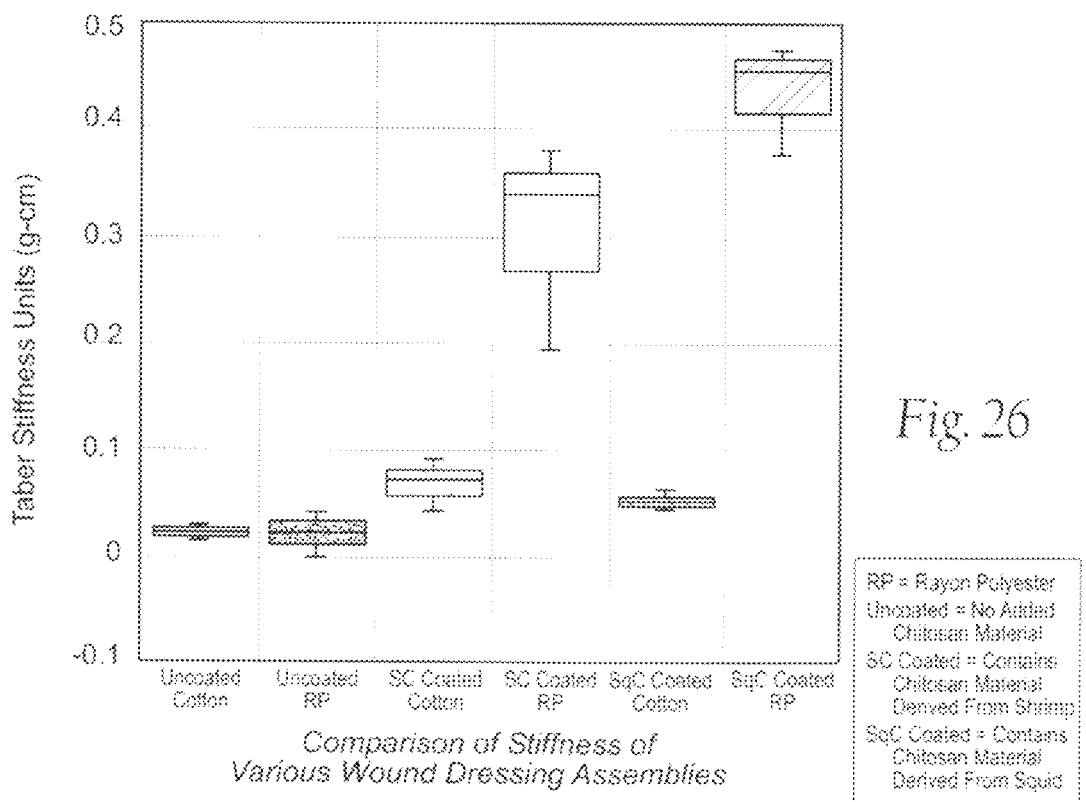
FIG. 26 is a graph comparing various dressing assemblies and the flexibility of those dressing assemblies based on values for the Taber Stiffness Scale.

FIG. 26 compares dressing assemblies of the present invention to prior dressing assemblies to determine the stiffness of the assemblies. The flexibility does not affect the efficacy of the assemblies themselves, but is more relevant when treating wounds as discussed, above. Stiffness can be expressed in terms of a ratio between the Tabor stiffness value (in units of milligrams) (as determined when dry by using a Taber Stiffness Tester Model 150E manufactured by Taber Industries of Buffalo, N.Y.).

Comparisons were made between dressing assemblies that did not comprise any chitosan material (Uncoated) and dressing assemblies that contained chitosan materials (Coated), including different types of starting materials for the production of the chitosan (shrimp and squid). In addition, different materials were used for the carrier strip, as well (cotton and rayon polyester).

The wound dressing assemblies of the present invention were determined to have a degree of stiffness between about 30 and 2000 times of previously manufactured chitosan wound dressings, without a loss in the hemostatic properties of the assemblies. While both the dressing assemblies (cotton and rayon/polyester) containing a chitosan material had increased stiffness over the dressing assemblies that did not contain any chitosan material (i.e. Uncoated), the dressing assemblies that comprised a rayon/polyester carrier in combination with the chitosan material, as expected, showed higher stiffness compared to the Uncoated dressing assemblies.

D. Results

Example 3

A wound dressing assembly as prepared according to Example 1, above was tested to determine its ability to control hemorrhaging. An auxillosubclavian injury was created in a porcine model. The injury was created with a 2-cm skin entry and was approximately 10-cm deep from the skin to the axillary artery. The axillary artery was trimmed to 3 cm length and dilated with vasodilator (1% lidocaine/paravine solution, having a 4:1 v/v ratio). A 4-mm diameter perforation injury was created in front of the axillary artery using a 4 mm vascular punch, from Ethicon, in N.J. The wound dressing was applied through the 2-cm entry to fill and pack in the wound under manual pressure for 3 minutes. After pressure was released the hemorrhaging from the wound was controlled.

FIG. 27 provides further comparison and results of dressing assemblies of the present invention compared to similar prior art dressing assemblies, i.e. control assemblies. FIGS. 28-43 provide various SEM images of the dressing assemblies, both prior to and after interacting with blood. Various qualities of the dressing assemblies were compared, such as stiffness, permeability, absorbance, and other qualities.

Referring to FIG. 27, a carrier strip comprising a blend of 30% rayon and 70% polyester, sold by Johnson & Johnson, Inc. under the trademark Kling® was tested, both without the addition of a chitosan material (J & J Kling Roll (uncoated)) and with chitosan material added according to the present invention (100808, 120808, 08-XL-045). The uncoated carrier strip was used as a control. Each of the three dressing assemblies coated with chitosan exhibited improved qualities when compared to the control. For example, the three assemblies showed a significant increase in stiffness, an increase in the Single Drop Absorption Time (i.e., the contact angle), and an increase in the number of blood cells accumulated in the dressing assemblies.

The various characteristics in FIG. 27 demonstrate the improvement of the present invention over the prior assemblies. For example, when comparing the stiffness of each of the dressings of the present invention (100808, 120808, 08-XL-045) to the prior art assembly (J & J Kling Roll (uncoated)) the stiffness (Gurley units, mg) is approximately 10 times stiffer in the width direction (60-70 compared to 5 for the prior art), respectively compared to the prior art and 5 times stiffer in the machining length directions compared to the prior art (20-40 compared to 5 for the prior art), respectively. The increased stiffness improves the ease of application.

Similarly, the contact angle, blood absorbance capacity, and permeability for the dressing assemblies demonstrates improved structures for the present invention compared to the prior dressing assemblies. The contact angle (measured as the time that a sessile 20 μl decreases in volume to 5 μl drop) is 5× to 20× longer for the present invention compared to the prior art, 25-130 seconds and <5 seconds, respectively.

Table 2, below, shows the blood absorbance capacity (grams of blood/grams dressing) for the present invention compared to the prior art invention, after a 2 minute interval. Each of the assemblies 20 of the present invention is lower than that of the prior art, but provides sufficient absorbance capacity values.

TABLE 2

Blood Absorbance Capacity After 2 Minutes

| SAMPLE # | 120808 | 08-XL-045 | 100808 | J&J Kling (Prior Art) |
|---|---|---|---|---|
| AVG | 6.4 | 10.4 | 2.9 | 14.0 |
| STD DEV | 3.9 | 0.9 | 1.6 | 0.2 |

$p<0.05$ for all present art compared to prior art

The permeability of blood (defined as the mean flow rate mL/sec of blood through the specimen) (see FIG. 27) is approximately four (4) slower for the invention compared to the prior art, 0.2 (avg.) and 0.8, respectively. The improved structural characteristics of the present invention compared to the prior art assemblies accelerate clot formation and hemostasis. Slow penetration allows cells to concentrate and then as they slowly permeate through the structure clot formation occurs.

Figure 39:
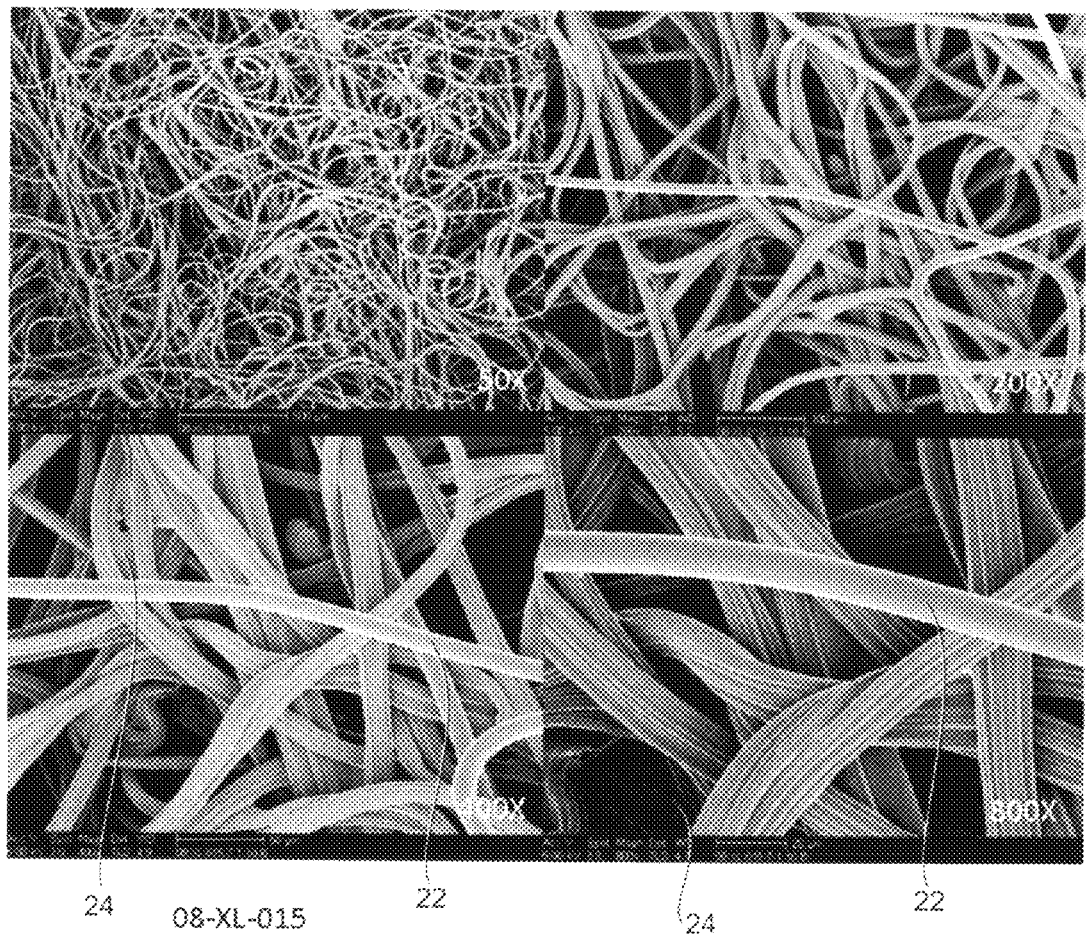

The improved ability of the dressing assemblies of the present invention are further demonstrated by comparing scanning electron micrograph (SEM) images of the dressing assemblies. Images of the J & J Kling Roll (uncoated) dressing assembly are shown in FIG. 39 after the dressing assembly has interfaced with blood. Very few blood cells are shown coagulating within the dressing assembly.

Figure 29:
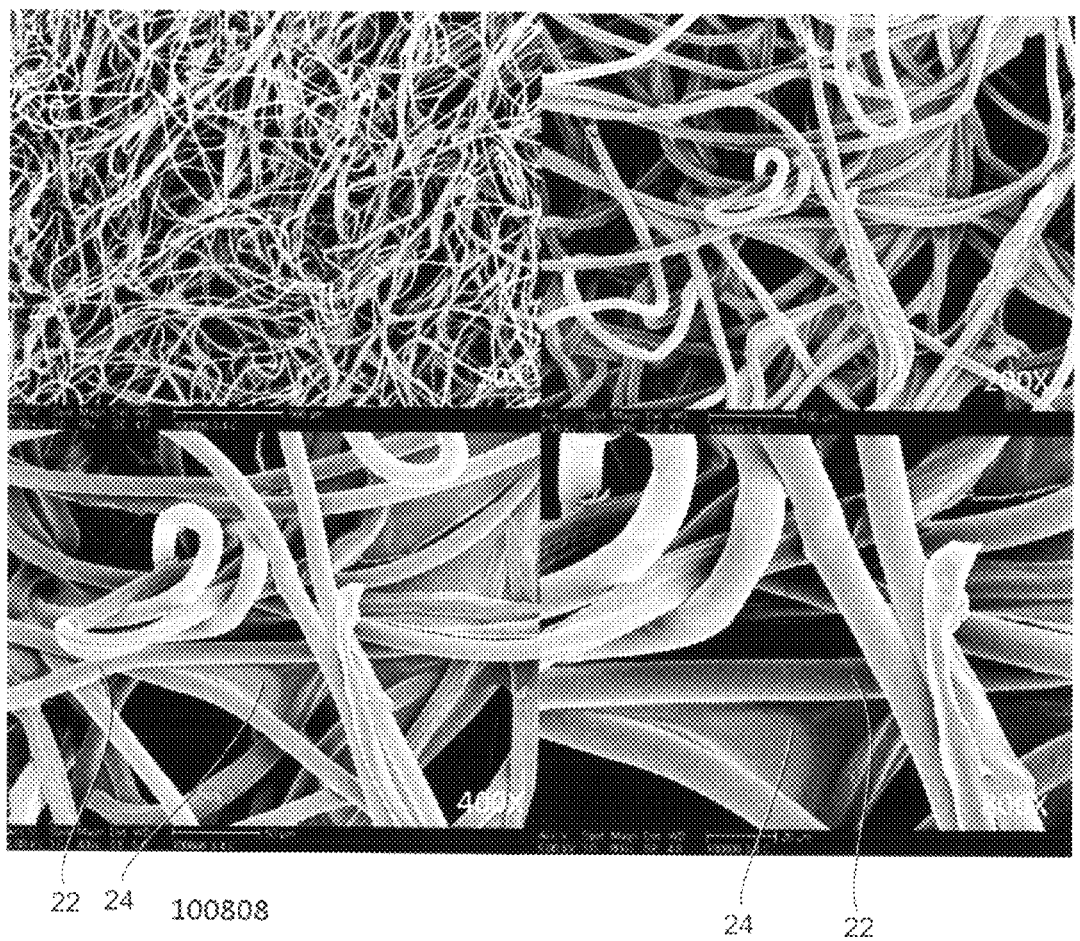
Figure 36:
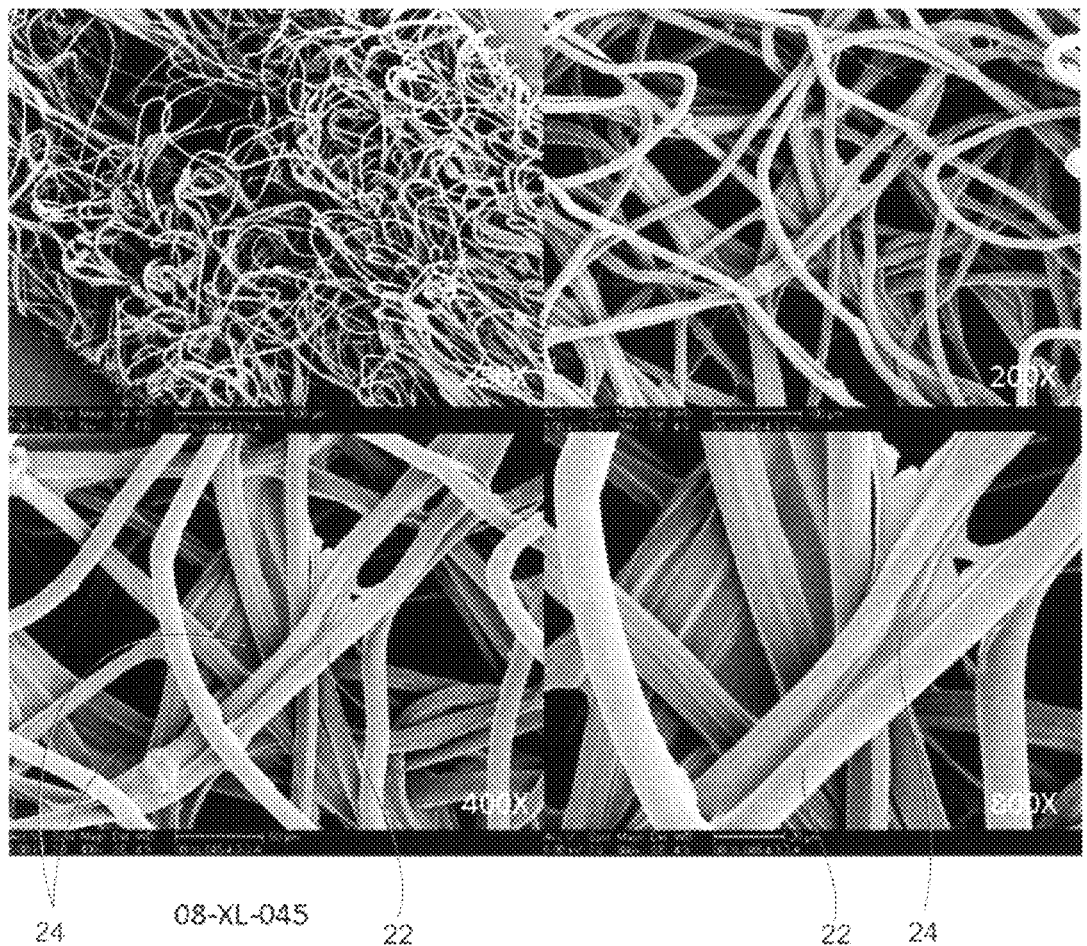
Figure 37:
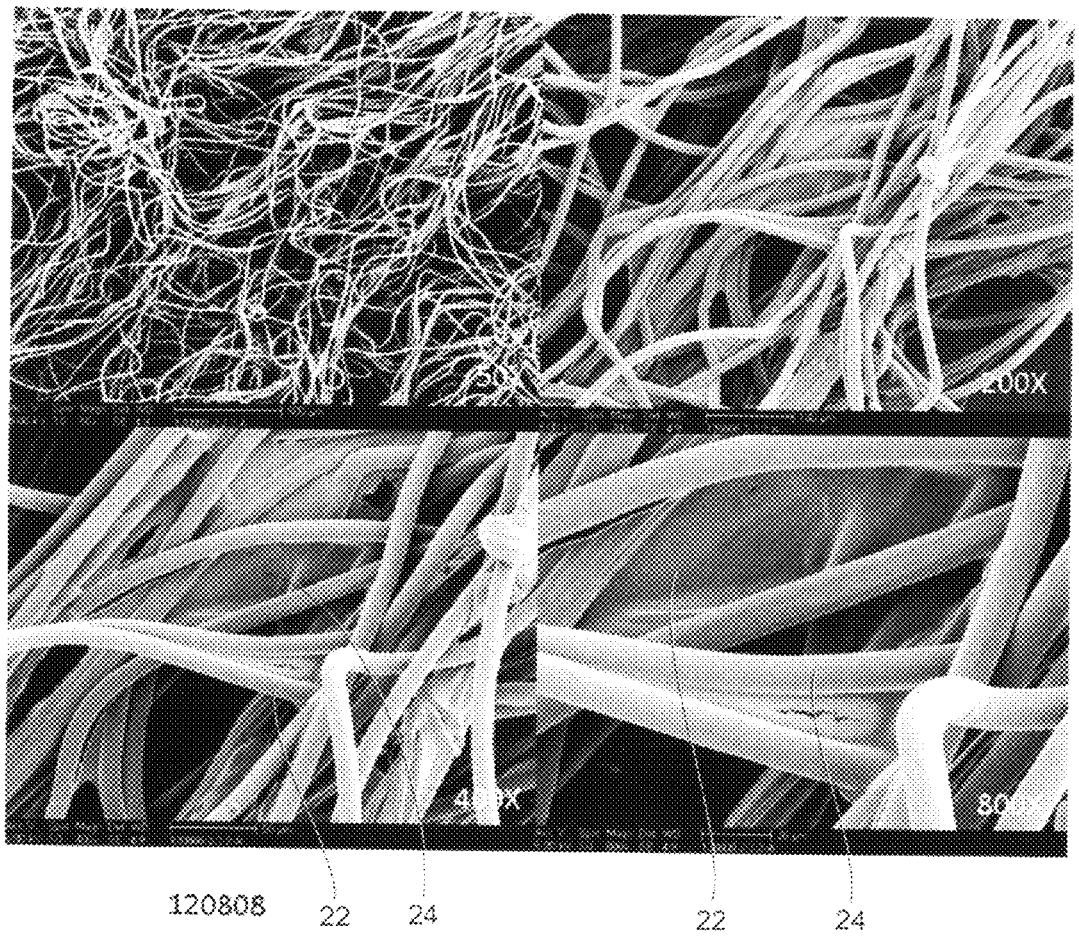
Figure 38:
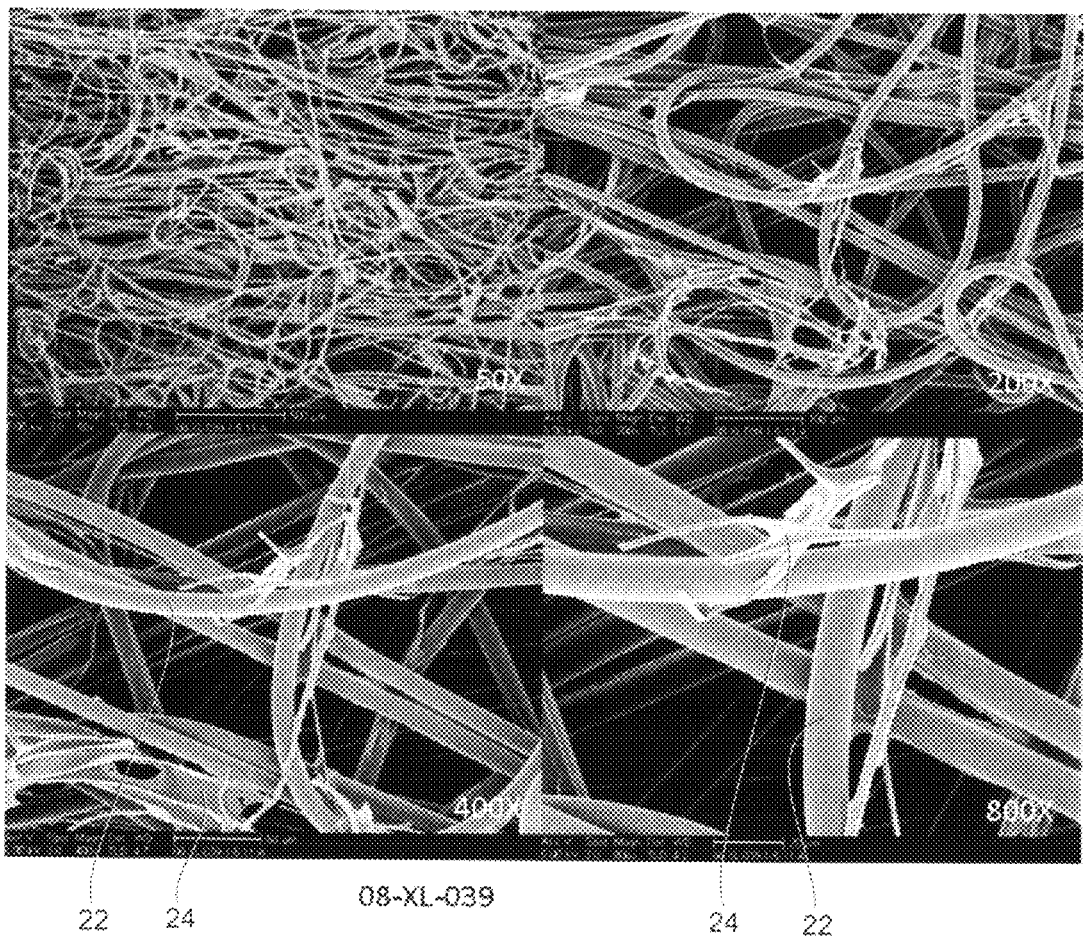

Conversely, the three assemblies of the present invention (100808, 120808, 08-XL-045) are capable of significant blood cell coagulation within the dressing assemblies. The three assemblies are shown in FIGS. 29, 37, and 36, respectively, prior to interfacing with blood, and FIGS. 41, 42, and 43, respectively, after the assemblies have interfaced with blood. The webs of chitosan material 24 extending between the individual fibers of the carrier strip 22 provide membranes that will allow collection and coagulation of the blood cells within the dressing assemblies 20, demonstrating a visible improvement over the prior art dressing assemblies.

Figure 28:
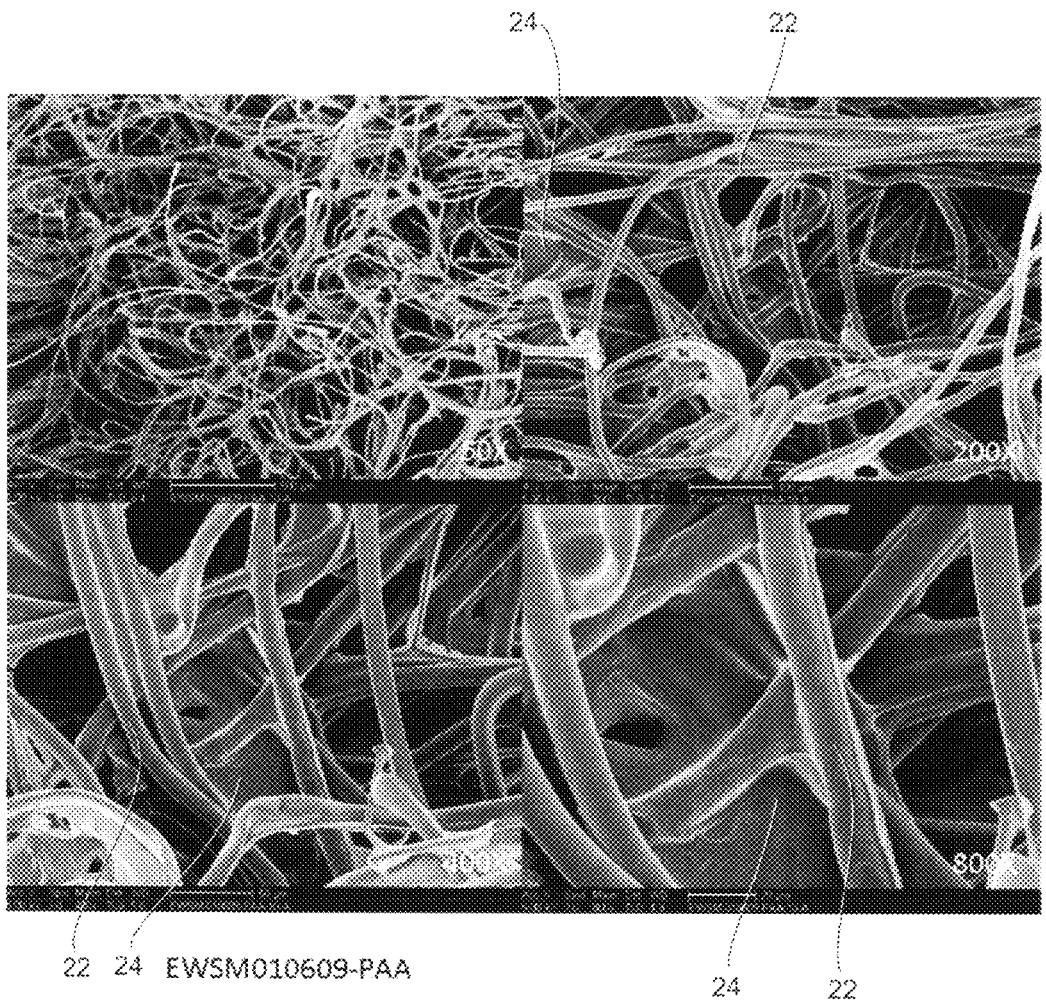
FIGS. 28-39 are various scanning electron micrograph (SEM) images of various wound dressing assemblies comprising various carrier strips.

The SEM images provide other possible dressing assemblies and compositions that could be formed according to the present invention. FIG. 28 shows and a dressing assembly as depicted and described with respect to FIG. 16. That is, the dressing assembly includes an adhesive material, i.e. polyacrylic acid. The carrier strip 22 comprises 30% rayon and 70% polyester. The SEM image shows relatively robust areas of chitosan material 24 within the dressing assembly.

Figure 30:
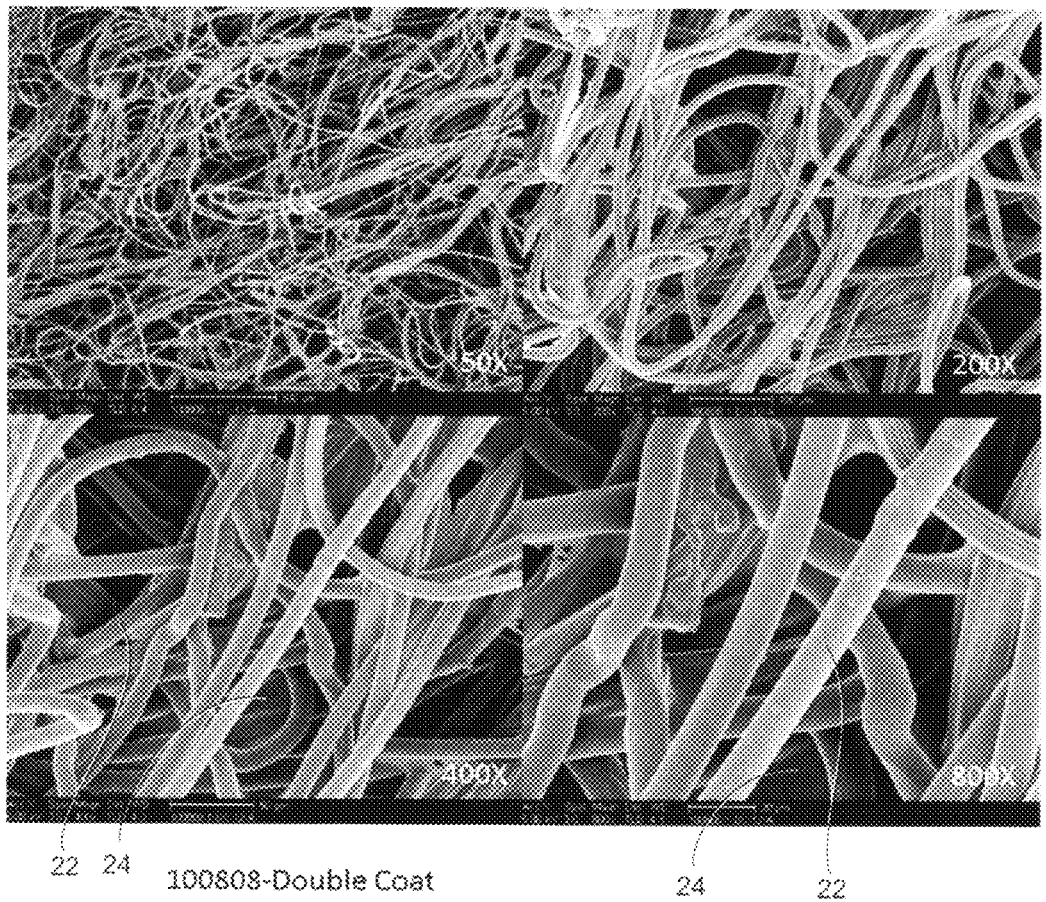
Figure 31:
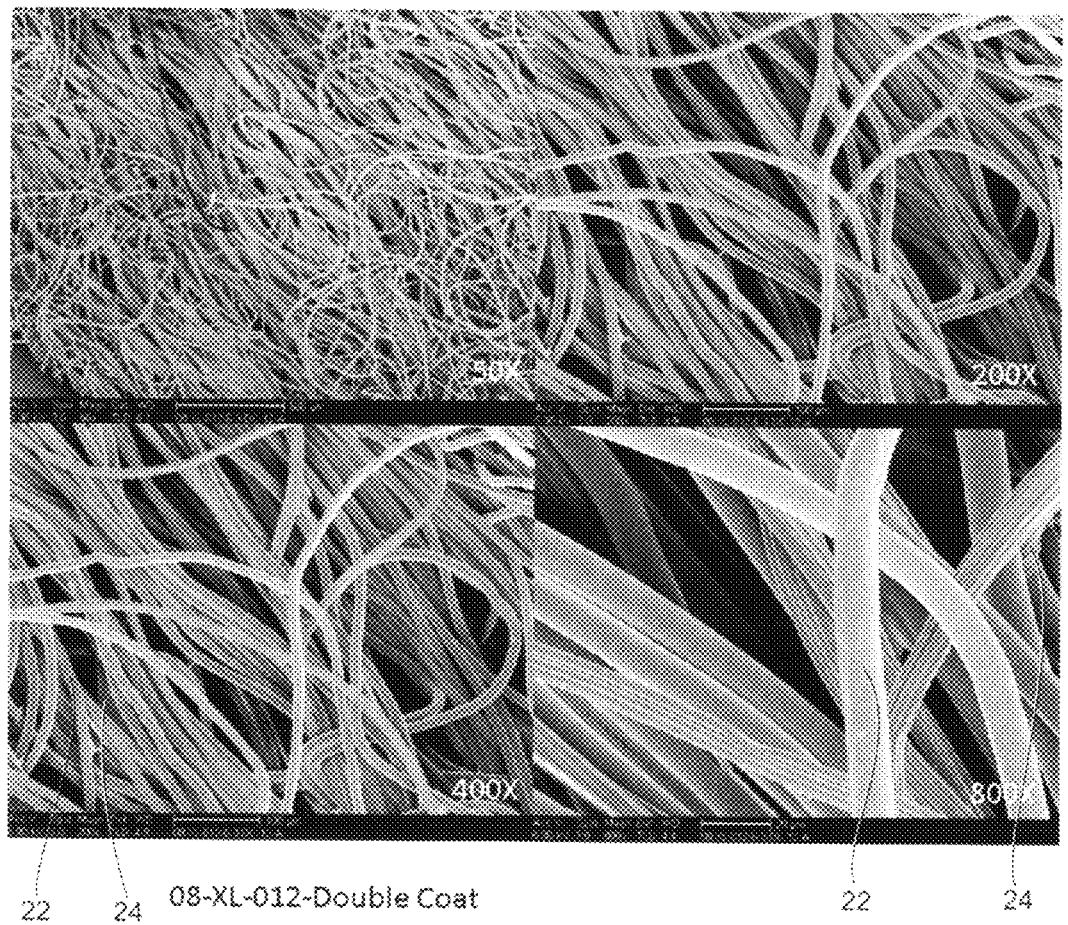
Figure 32:
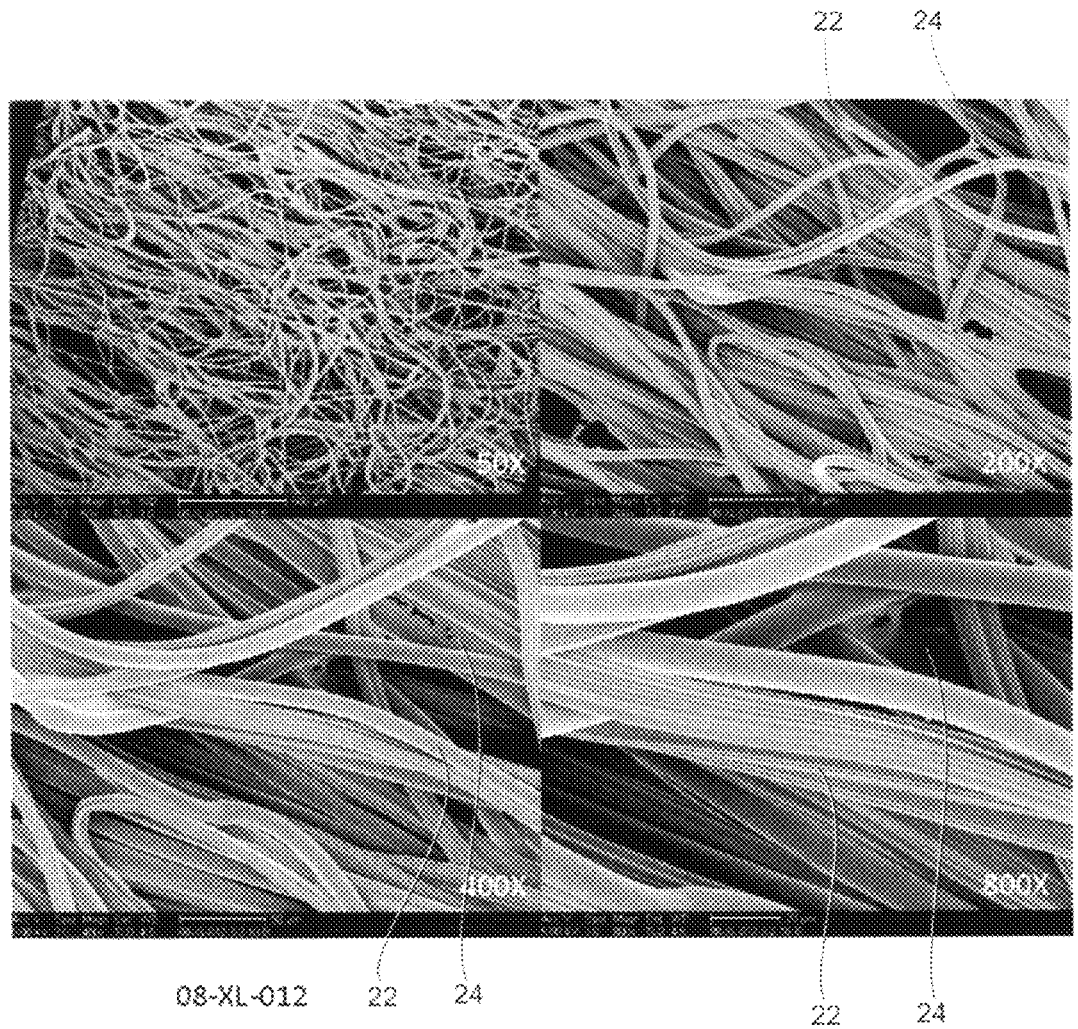
Figure 33:
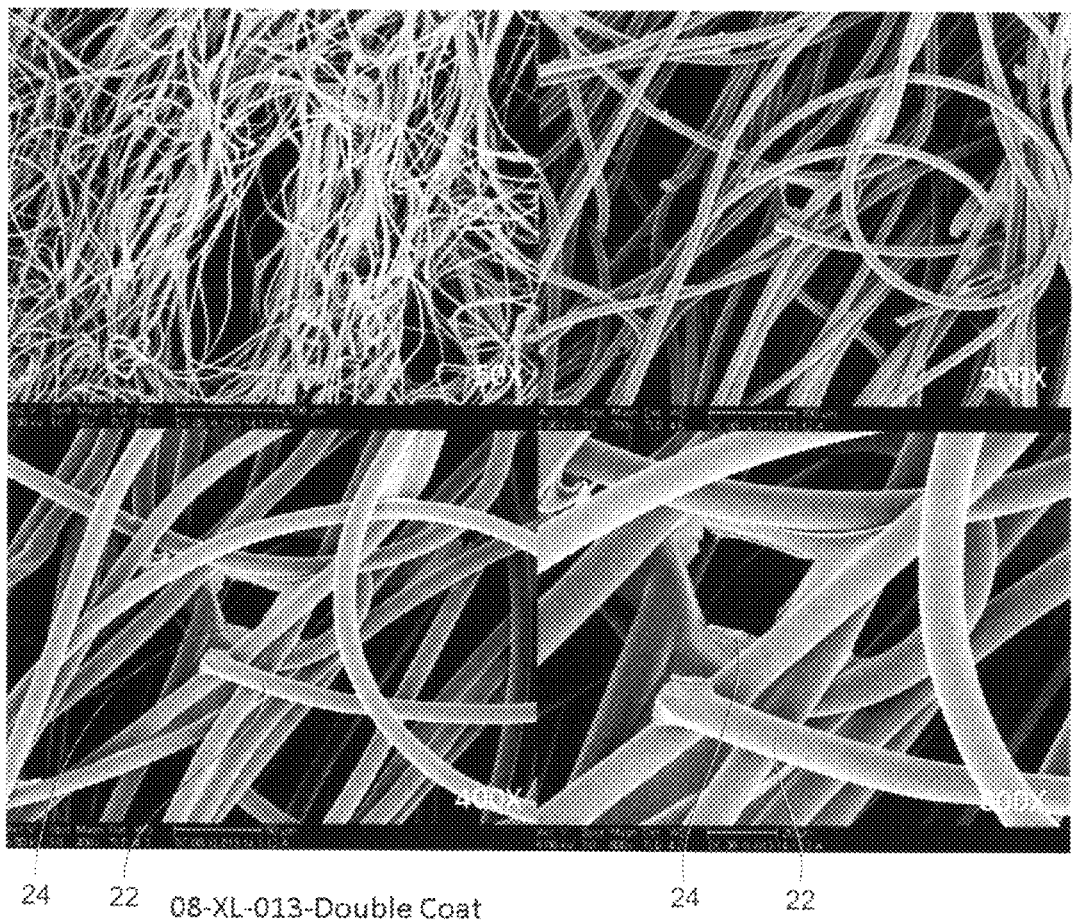
Figure 34:
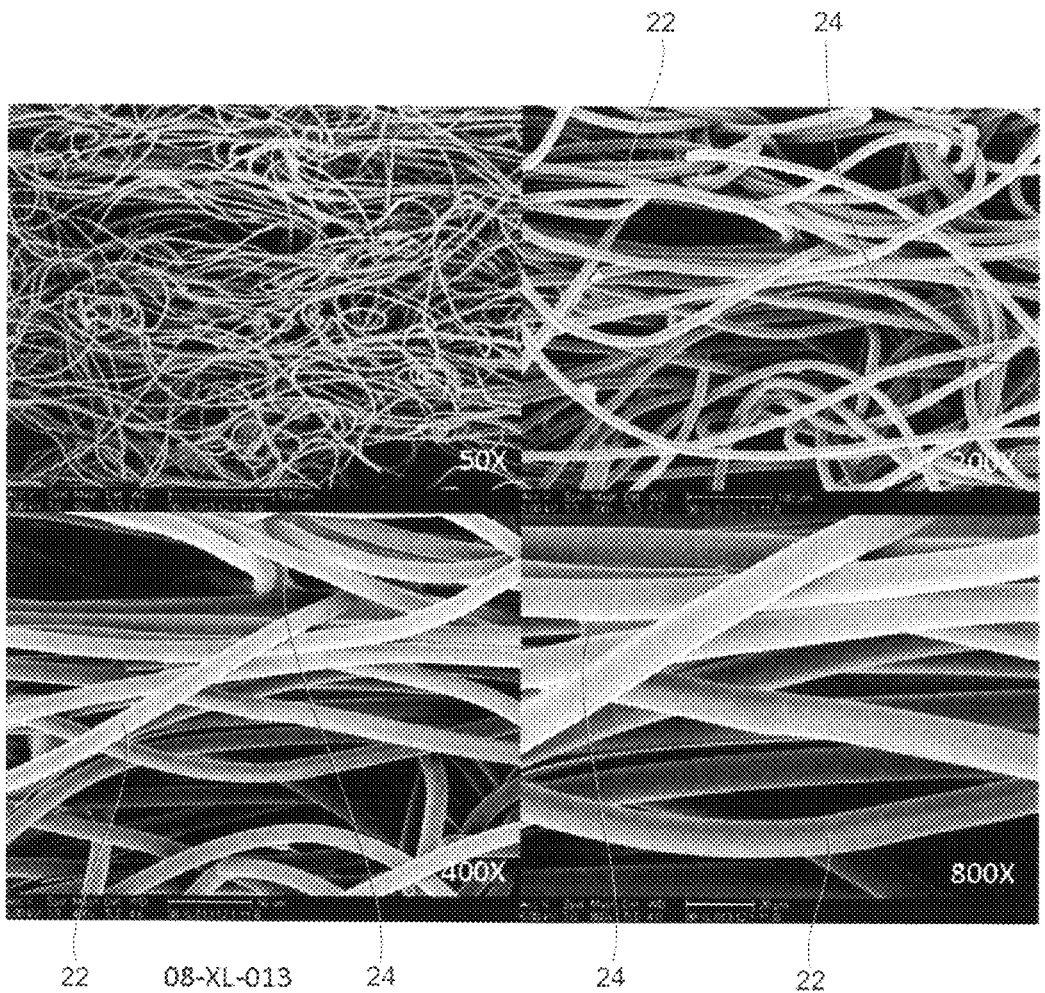

FIGS. 30, 31, and 33 contemplate dressing assemblies wherein the preparatory step of applying chitosan material has been repeated, or the carrier strip 22 has been "double coated" with chitosan material.

Figure 35:
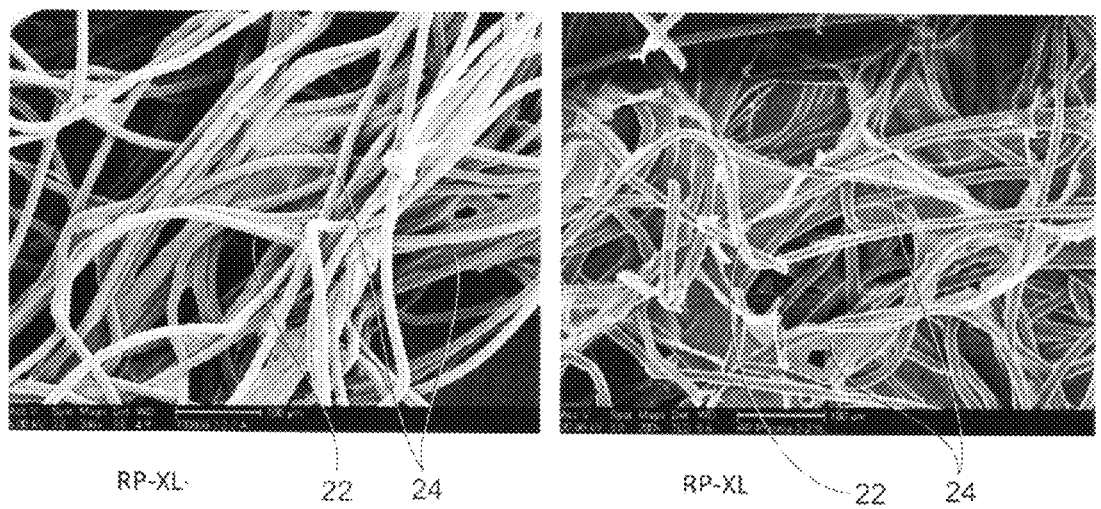

Alternative additives or material may be added to the dressing assembly of the present invention. For example, FIG. 35 depicts a dressing assembly comprising chitosan material and a carrier strip that has been further treated with a plasma material.

FIG. 39 depicts a dressing assembly having a carrier strip 22 comprised of 70% rayon and 30% polyester.

E. Other Uses of the Wound Dressing Assembly

The wound dressing assemblies of the present invention can also be incorporated for other uses. For example, the wound dressing assembly can be used to form an anti-microbial barrier; or to form an antiviral patch; or to intervene in a bleeding disorder; or to release a therapeutic agent; or to treat a mucosal surface; or to dress a staph or MRSA infection site; or in various dental surgical procedures, or combinations thereof.

For example the wound dressing assembly may further comprise an active ingredient. The active ingredient may include, but is not limited to, calcium, thrombin, factor VIIa, factor XIII, thromboxane A2, prostaglandin-2a, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibrobast growth factor, keratinocyte growth factor, nerve growth factor, penicillin, ampicillin, methicillin, amoxycillin, clavamox, clavulanic acid, amoxicillin, aztreonam, imipenem, streptomycin, Kanamycin, Tobramycin, gentamicin, vancomycin, clindamycin, erythromycin, polymyxin, hacitracin, amphotericin, nystatin. rifampicin, tetracycline, doxycycline, chloramphenicol, vasoconstrictors, e.g. epinephrine and histamines, and combinations thereof.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A hemostatic article comprising:
a nonwoven mesh composed of fibers of a polymeric material, wherein the polymeric material is a blend of rayon and polyester; and
an interpenetrating network of a dried chitosan solution, wherein the interpenetrating network is in the form of webs anchored among various fibers of the polymeric material and wherein the dried chitosan solution has a moisture content of less than 4.36 weight percent; and
wherein the hemostatic article has a permeability to blood (mean flow rate) of 0.15-0.35 ml/s and a Gurley stiffness value (in units of milligrams) of 500-6,000.

2. The hemostatic article of claim 1, wherein the weight ratio of rayon to polyester in the polymeric material is in the range of from about 1:3 to about 3:1.

3. The hemostatic article of claim 1, wherein the weight ratio of rayon to polyester in the polymeric material is in the range of from about 1:4 to about 3:4.

4. The hemostatic article of claim 1, wherein the dried chitosan solution has a moisture content of less than 3.12 weight percent.

5. The hemostatic article of claim 1, wherein the dried chitosan solution has an acid content of 1.8-2.1 weight percent.

6. A wound dressing assembly comprising the hemostatic article of claim 1 and an adhesive layer.

\* \* \* \* \*